(12) United States Patent
Asrar et al.

(10) Patent No.: US 7,098,170 B2
(45) Date of Patent: Aug. 29, 2006

(54) METHOD OF IMPROVING YIELD AND VIGOR OF PLANTS BY TREATMENT WITH TRIAZOLE AND STROBILURIN-TYPE FUNGICIDES

(75) Inventors: Jawed Asrar, Chesterfield, MO (US); Ernest F. Sanders, St. Louis, MO (US); Yiwei Ding, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 12 days.

(21) Appl. No.: 10/081,023

(22) Filed: Feb. 21, 2002

(65) Prior Publication Data

US 2003/0060371 A1 Mar. 27, 2003

Related U.S. Application Data

(63) Continuation-in-part of application No. 10/026,301, filed on Dec. 19, 2001.

(60) Provisional application No. 60/257,502, filed on Dec. 22, 2000.

(51) Int. Cl.
*A01N 43/28* (2006.01)
*A01N 43/54* (2006.01)
*A01N 43/653* (2006.01)
*A01N 55/10* (2006.01)
*A01P 21/00* (2006.01)

(52) U.S. Cl. .................... 504/242; 504/243; 504/254; 504/270; 504/272; 504/282; 504/336; 514/383; 514/407

(58) Field of Classification Search ............ 504/261, 504/272, 275, 280, 242, 243, 270, 282, 336, 504/254; 514/383, 407
See application file for complete search history.

(56) References Cited

U.S. PATENT DOCUMENTS

| | | | |
|---|---|---|---|
| 4,510,136 A | 4/1985 | Moberg | 514/63 |
| 4,861,367 A * | 8/1989 | Nyfeler et al. | 71/92 |
| 5,145,856 A | 9/1992 | Clough et al. | 514/274 |
| 5,264,440 A | 11/1993 | Clough et al. | 514/269 |
| 5,288,747 A * | 2/1994 | Aebi et al. | 514/383 |
| 5,306,712 A | 4/1994 | Tobitsuka et al. | 514/63 |
| 5,395,825 A | 3/1995 | Clough et al. | 514/269 |
| 5,468,747 A | 11/1995 | Clough et al. | 514/239.5 |
| 5,482,974 A | 1/1996 | Phillion et al. | 514/619 |
| 5,486,621 A | 1/1996 | Phillion et al. | 549/4 |
| 5,489,606 A | 2/1996 | Oida et al. | 514/383 |
| 5,498,630 A | 3/1996 | Phillion et al. | 514/443 |
| 5,693,667 A | 12/1997 | Phillion et al. | 514/461 |
| 5,705,513 A | 1/1998 | Phillion et al. | 514/354 |
| 5,739,140 A | 4/1998 | Clinton et al. | 514/269 |
| 5,811,411 A | 9/1998 | Phillion et al. | 514/63 |
| 5,834,447 A | 11/1998 | Phillion et al. | 514/63 |
| 5,849,723 A | 12/1998 | Phillion et al. | 514/63 |
| 5,977,152 A | 11/1999 | Oida et al. | 514/383 |
| 5,994,270 A | 11/1999 | Phillion et al. | 504/193 |
| 5,998,466 A | 12/1999 | Phillion et al. | 514/443 |
| 6,028,101 A | 2/2000 | Phillion et al. | 514/469 |
| 6,617,330 B1 * | 9/2003 | Walter | 514/258.1 |

FOREIGN PATENT DOCUMENTS

| | | | |
|---|---|---|---|
| EP | 067479 | * | 6/1982 |
| EP | 0538231 A1 | | 10/1992 |
| EP | 0382375 B1 | | 3/1994 |
| EP | 0 622 020 | * | 4/1994 |
| WO | WO 93/07751 | | 4/1993 |

OTHER PUBLICATIONS

Tsuda et al, Simeconazole, a novel systemic fungicide, 2000, BCPC Conference—Pests & Diseases, vol. 2 pp. 557-562.*
"A Guide to Take-All, A Disease in Cereal Grains," MONSANTO FOOD HEALTH HOPE™, 1998, downloaded from website address www.takeall.com on Nov. 4, 2000.
Anderson, J.M., et al, "Items for the United States—Indiana," ANNUAL WHEAT NEWSLETTER, vol. 46, U.S.A., downloaded from website address wheat.pw.usda.gov. on Nov. 9, 2000.
"Crop Profile for Soybeans in Illinois," USDA OPMP & PIAP, Feb. 2000, downloaded from website address pestdata.ncsu.edu/crop-profiles on Nov. 4, 2000.
"Crop Profile for Soybeans in Iowa," USDA OPMP & PIAP, Feb. 1999, downloaded from website address pestdata.ncsu.edu/crop-profiles on Nov. 4, 2000.
"Monsanto launches wheat disease remedy in Ireland," IRISH BIOTECH NEWS, Oct. 1999, No. 55, downloaded from website address www.biores-irl.ie on Nov. 9, 2000.
*The Pesticide Manual: Twelfth Edition*, United Kingdom, The British Crop Protection Council, C.D.S. Tomlin, Ed., 2000, various pages from 33 through 951.

(Continued)

*Primary Examiner*—S. Mark Clardy
(74) *Attorney, Agent, or Firm*—Nelson Mullins Riley & Scarborough LLP

(57) ABSTRACT

A method of improving the yield and vigor of an agronomic plant involves treating plants such as soybeans and corn and/or their propagation material with a composition that includes an active agent, such as a diazole fungicide, a triazole fungicide, or a strobilurin-type fungicide, which has the capacity to improve the yield and/or the vigor of the plant in the absence of pest pressure by fungal plant pathogens. Formulations that contain a diazole fungicide, a triazole fungicide, or a strobilurin-type fungicide, and plants and plant propagation material, such as seeds, which have been treated by the novel method are also described.

82 Claims, No Drawings

OTHER PUBLICATIONS

"Rival & Allegiance-FL," AGRIPROTREAT, downloaded from website address www.agripro.com/seeds/Treatments on Nov. 9, 2000.

Wiesbrook, Michelle, "Agronomic," ILLINOIS PESTICIDE REVIEW, vol. 2001, issue 5, Sep. 2001, U.S.A., downloaded from website address www.aces.uiuc.edu on Feb. 14, 2002.

Wiesbrook, Michelle, "Agronomic," ILLINOIS PESTICIDE REVIEW, vol. 1999, issue 5, Sep. 1999, U.S.A., downloaded from website address www.aces.uiuc.edu on Nov. 9, 2000.

English translation of European Patent Application Publication No. 0 622 020 A1, Apr. 22, 1994, Gatineau, et al.

* cited by examiner

METHOD OF IMPROVING YIELD AND VIGOR OF PLANTS BY TREATMENT WITH TRIAZOLE AND STROBILURIN-TYPE FUNGICIDES

CROSS-REFERENCE TO OTHER PATENTS AND PATENT APPLICATIONS

The present application claims priority to co-pending and commonly assigned U.S. patent application Ser. No. 10/026,301, that was filed on Dec. 19, 2001, which claimed priority to U.S. Provisional Patent Application Ser. No. 60/257,502 which was filed on Dec. 22, 2000, each of which is incorporated by reference herein in its entirety.

BACKGROUND OF THE INVENTION (1) Field of the Invention

The present invention relates to the improvement of the yield and vigor of agronomic plants, and more particularly to a method of improving the yield and vigor of agronomic plants by treatment of the plant or its propagation material with certain active agents.

(2) Description of the Related Art

Plants, and in particular, legumes, are a critical source of food, animal feed, fiber, and useful chemicals and medicaments. The ability of legumes to fix nitrogen provides this order of plants with the unusual ability to provide high quality nutritional proteins as well as to improve the nitrogen content of the soils in which they grow. One species of legume—the soybean—is an ancient and important worldwide crop. Relatively easy to grow and subject to relatively few important insect pests, compared with other important agronomic crops, soybeans provide oil and high protein meal for human and animal consumption and for industrial uses.

In the United States, about 70 million acres are planted to soybeans each year and recent annual soybean production has been over 2.5 billion bushels. The average yield of soybeans in the United States has been steadily increasing over the past 75 years from an initial level of about 11 bu/ac, to the present level of about 35 to 40 bu/ac. (See, *United States Department of Agriculture, National Agricultural Statistics Service, Crop Report*, June 2000, Washington, D.C.). Better strains of seed and the systematic improvement of agricultural and pest management practices have facilitated this improvement.

Where the growing season permits in the Midwestern United States, soybeans are typically grown in rotation with field corn and sometimes in a double-crop after winter wheat is harvested. Conservation tillage practices are regularly used for soybeans and from one-fourth to about one-third of the acreage is no-tilled. About two-thirds of all soybeans are solid seeded (sown in narrow, 6", 7", or 8" rows). The benefits of solid seeding a soybean crop are that the canopy closes quickly and can reduce weed growth and, hence the need for late season post emergence herbicides. This eliminates the possibility of row cultivation and late season application of pesticides by ground application.

In the U.S. Midwest, soybeans are rarely treated for insect pests, and the few insects that can cause crop loss include bean leaf beetle (*Cerotoma trifurcata*), grasshoppers (*Melanoplus* spp.), green cloverworm (*Plathypena scabra*), and potato leafhopper (*Empoasca fabae*).

Soybean yield can be adversely affected by several diseases, and among these are pythium damping off (*Pythium* spp.), phytophthera damping off (*Phytophthera* spp.), rhizoctonia root rot (*Rhizoctonia solani*), anthracnose (*Colletotrichum* spp.), stem canker (*Diaporthe phaseolorum*), septoria leaf spot (*Septoria glycines*), purple seed stain (*Cercospora kikuchii*), sudden death syndrome (*Fusarium solani*), white mold (*Sclerotinia sclerotinorum*), and brown stem rot (*Phialophora gregata*). It is known, however, that non-pesticidal management measures are equal to or better than pesticides for the control of many common pathogens. Plant disease management for soybeans has always relied more on agronomic practices than on pesticides, and seed treatment and foliar fungicides, along with nematicides, play a limited role. (See, e.g., information dealing with soybeans on U.S. Department of Agriculture website: http://pestdata.ncsu.edu/cropprofiles/, dated Nov. 4, 2000).

Diseases such as "Take-all disease", caused by the organism *Gaeumannomyces graminis*, which are prevalent in cereal crops, have not been reported to affect soybeans.

Seed treatment with fungicides, such as metalaxyl, carboxin, captan and thiram, which are active against the known soybean disease-causing organisms listed above, is common for soybeans, and the impact of fungicidal seed treatment on yield due to the avoidance of stand losses due to these diseases is significant. However, the cost of such seed treatment is modest relative to overall production costs. Moreover, since several fungicides are approved for use on soybeans, if one or two of the fungicides were to be withdrawn, it is likely that one or more other known compounds would be adequate substitutes. Therefore, the incentive to search for different fungicides to act as fungicidal seed treatment compounds for soybeans has been slight.

However, with the limited amount of high quality arable land that is available for row crop production in regions having suitable climate, any method that would improve the vigor and yield of agronomic plants in general, and in particular, for legumes, such as soybeans, would provide a significant advantage. It would be particularly useful if such method was easy to apply.

SUMMARY OF THE INVENTION

Briefly therefore, the present invention is directed to a novel method of increasing the vigor and/or the yield of an agronomic plant comprising treating the plant or its propagation material with an effective amount of an active agent which has the capability of increasing the yield and/or vigor of the plant in the absence of pest pressure by fungal plant pathogens, where the active agent is selected from the group consisting of a diazole fungicide, a triazole fungicide, and a strobilurin-type fungicide.

The present invention is also directed to a novel method of increasing the vigor and/or the yield of an agronomic plant except for wheat comprising treating an agronomic plant or its propagation material except for wheat with a composition comprising an effective amount of an active agent that has activity against *Gaeumannomyces graminis*, where the active agent is selected from the group consisting of a diazole fungicide, a triazole fungicide, and a strobilurin-type fungicide.

The present invention is also directed to a novel method of improving the vigor and/or the yield of an agronomic plant, the method comprising treating an agronomic plant or its propagation material with an amount of a diazole, triazole or strobilurin-type fungicide that is sufficient to improve the yield and/or the vigor of the agronomic plant, wherein common agricultural practice for the agronomic plant does not include treatment of the plant or its propagation material with a diazole, triazole or strobilurin-type fungicide.

The present invention is also directed to a novel method of increasing the vigor and/or the yield of an agronomic plant comprising treating the plant or its propagation material with an effective amount of a diazole fungicide, a triazole fungicide, or a strobilurin-type fungicide, which has the capability of increasing the yield and/or vigor of the plant in the substantial absence of pest pressure by fungal plant pathogens.

The present invention is also directed to a novel method of increasing the vigor and/or the yield of an agronomic plant comprising treating the plant or its propagation material with an effective amount of a diazole fungicide, a triazole fungicide, or a strobilurin-type fungicide, which has the capability of increasing the yield and/or vigor of the plant in a test wherein germination, sprouting and growth of the plant is carried out under substantially sterile conditions.

The present invention is also directed to a novel agronomic plant or its propagation material for which *Gaeumannoyces graminis* is not a disease-causing organism, wherein the plant or its propagation material has been treated with a composition comprising an effective amount of an active agent which has activity against *Gaeumannoyces graminis*, and wherein the plant is not wheat and the active agent is selected from the group consisting of a diazole fungicide, a triazole fungicide, and a strobilurin-type fungicide.

The present invention is also directed to a novel plant or its propagation material of the family Fabaceae which has been treated with a composition comprising an active agent which has activity against *Gaeumannoyces graminis* in an amount sufficient to increase the yield and/or the vigor of said plant, wherein the active agent is selected from the group consisting of a diazole fungicide, a triazole fungicide, and a strobilurin-type fungicide.

The present invention is also directed to a novel seed that has been treated by any one of the methods described above.

Among the several advantages found to be achieved by the present invention, therefore, may be noted the provision of a method that improves the vigor and yield of agronomic plants in general, and in particular, for legumes, such as soybeans, the provision of a such a method that is easy to apply.

DETAILED DESCRIPTION OF THE PREFERRED EMBODIMENTS

In accordance with the present invention, it has been discovered that the vigor and/or the yield of an agronomic plant can be increased by treating the seed and/or the foliage of the plant with an effective amount of an active agent, in particular a diazole fungicide, a triazole fungicide, or a strobilurin-type fungicide, which has the capability of causing an improvement in the vigor and/or the yield of the plant whether or not the plant is under pest pressure from fungal pathogens. In particular, this effect is noted when the plant is not under pest pressure from fungal pathogens of the type against which the diazole, triazole, or strobilurin-type fungicide is known to have activity. In preferred embodiments, in fact, the increase in yield and/or vigor can be shown to take place even when the treated seed and plant are under no pest pressure, for example, as in tests where germination, sprouting and plant growth take place under substantially sterile conditions.

The increase in yield and/or vigor is entirely unexpected because it is brought about by fungicides, but can occur even in the absence of pest pressure by fungal pathogens against which the fungicide is known to be active. By way of example, the method is useful to increase plant vigor and/or yield in geographic areas, or with cultivation practices, where the particular fungicide is not normally used—and even under conditions where the fungicide has no activity against the fungal pathogens that are known to be harmful to the plant.

In fact, it is believed that it would be counterintuitive for someone having skill in the art of controlling fungal pathogens in crops to apply an agent to a plant—at not inconsiderable expense—in instances where the known activity of the agent was believed not to be needed. In fact, given the care expended upon minimizing the use of resources in modern farming practices, such an application would be considered to be a waste. But, surprisingly, the inventors have found that this is not the case. The inventors have found that some fungicides—diazole fungicides, triazole fungicides, and strobilurin-type fungicides, in particular—can be applied to plant seeds, and in another embodiment to the plants themselves, with the result that the plants demonstrate increased yield and/or vigor.

It is also believed that the novel method demonstrates particularly useful and unexpected results in situations where the treated seed or plant is subjected to some stress during or after germination. For example, such stress could be caused by environmental stress, such as drought, cold, cold and wet, and other such conditions. It is believed, in fact, that side-by-side comparisons of plants grown from seeds treated by preferred embodiments of the novel method and plants grown from untreated seeds are subjected to drought conditions sometime after sprouting will demonstrate the superiority of the plants grown from the treated seeds.

When the plant is other than wheat, and in particular when the plant is of the family Fabaceae, treatment of the seed and/or the foliage of the plant with certain active agents that are known to have activity against the fungus *Gaeumannoyces graminis* (Gg), and, in particular against the Gg variety *tritici*, is believed to result in a surprising improvement in the yield and vigor of such plants. As discussed above, this improvement is unexpected because the improvement can occur even in plants for which *Gaeumannoyces graminis* var. *tritici* is not a known disease-causing agent. Nonetheless, it is believed that when these active agents are applied to soybeans, for example, the crop will show improvements in both yield and vigor. This effect is unexpected because the organism *Gaeumannoyces graminis* var. *tritici* is not known to have any detrimental effect on soybeans, and the active agent used to treat the soybeans has little activity against the commonly known disease-causing organisms for that crop.

Since the active agents that are useful in the novel method can be applied to plant propagation material such as seed prior to planting, the present method provides an easy method of achieving the advantages of improved plant yield and/or vigor without the added effort and expense of cultivation or in-field application after germination and sprouting.

Alternatively, the subject method can be applied to plants after they have sprouted, such as by foliar application by spraying or dusting. When this embodiment is used, the active agent can also be combined, if desired, with other agents, such as other herbicides or pesticides, to obtain further beneficial results. When the active agent is used with herbicides, it is preferred that the plant be a transgenic plant having a transgenic event that provides resistance to the particular herbicide being used.

When the terms "plant propagation material" is used herein, it is meant to include plant seeds, cuttings, sets, rhizomes, tubers, meristem tissue, single and multiple plant cells, and any other plant tissue from which a complete plant can be obtained.

When it is said that an active agent is known to "have activity against *Gaeumannoyces graminis*", it is meant that the agent has some degree of biostatic or biocidal activity against that organism when it is contacted with the organism under conditions that are conventionally employed for the determination of an $EC_{50}$ value for the agent upon that organism. As used herein, the term "$EC_{50}$" means the median effective concentration of an active agent against a particular organism. The method for determining the $EC_{50}$ value for a fungicide is described by Nuninger-Ney et al., In vitro test method for assessment of propiconazole sensitivity in *Pyrenophora teres* isolates, FRAC Methods for Monitoring Fungicide Resistance, EPPO Bulletin, 21:291–354 (1991). It is preferred that the active agent is one that has an $EC_{50}$ value against *Gaeumannoyces graminis* var. *tritici* of not over about 10 µg/ml, more preferred that the $EC_{50}$ value be not over about 1 µg/ml, even more preferred that the $EC_{50}$ value be not over about 0.1 µg/ml, and yet more preferred that the $EC_{50}$ value be not over about 0.01 µg/ml against *Gaeumannoyces graminis* var. *tritici*.

The active agent of one embodiment of the subject method can be one that not only has activity against *Gaeumannoyces graminis*, but also can have no significant activity against the diseases that are commonly known to attack the plant to be treated with the subject method. By way of example, a preferred active agent for use on soybeans is one having activity against *Gaeumannoyces graminis* var. *tritici*, but having no significant activity against one or more of such diseases as phytophthera damping off (*Phytophthera* spp.), rhizoctonia root rot (*Rhizoctonia solani*), anthracnose (*Colletotrichum* spp.), septoria leaf spot (*Septoria glycines*), pythium (*Pythium* spp.), and sudden death syndrome (*Fusarium solani*), which are diseases that are known to attack soybeans.

The active agent can also be a fungicide that has the capability of increasing the yield and/or vigor of a plant even in the absence of fungal pathogens against which the fungicide has fungicidal activity. In preferred embodiments, the fungicide is one that is capable of increasing the yield and/or the vigor of a plant even when the seed is germinated and sprouted and the plant is grown under sterile conditions. In other words, in the absence of any fungal pathogens at all. When it is said that the seed is germinated and sprouted and the plant is grown under sterile conditions, what is meant is that a seed, which has been subjected to a non-phytotoxic surface sterilization procedure, such as contact with 0.1%–0.15% sodium hypochlorite solution containing 0.5% household detergent for 10 minutes, followed with rinsing 3 times with sterile distilled water, other appropriate sanitization procedures as are known in the art, is planted in a growing medium that has been sterilized, or is otherwise substantially free of organisms that are pathogenic for the plant.

When a "fungal plant pathogen" is referred to, what is meant is a fungal strain known to be an important pathogen of a particular plant. For example, *Gaeumannoyces graminis* is a known plant pathogen for wheat.

When it is said that an active agent has only "weak, or no activity", or "no significant activity", against a certain disease-causing organism, what is meant is that the active agent is not sufficient to control the particular disease-causing organism when the active agent is applied to a plant or its propagation material in an amount that is within the range of currently acceptable practice for that active agent. It is preferred that an active agent having no significant activity against a disease-causing organism has an $EC_{50}$ value against such organism of over about 10 µg/ml, preferably greater than about 20 µg/ml.

As used herein, the terms "agronomic plant" and "agronomically important plant" mean the same thing, and both refer to a plant of which a part or all is, or has been, harvested or cultivated on a commercial scale, or serves as an important source of feed, food, fiber or other chemical compounds. Without limitation, some examples of such plants are corn, cereals, including wheat, barley, rye, and rice, vegetables, clovers, legumes, including beans, peas and alfalfa, sugar cane, sugar beets, tobacco, cotton, rapeseed (canola), sunflower, safflower, and sorghum. In an embodiment of the invention where the active agent is one that has activity against *Gaeumannoyces graminis*, wheat is not considered to be an agronomic plant for the purposes of this specification.

When the subject method is described herein as "increasing the yield" of an agronomic plant, what is meant is that the yield of a product of the plant is increased by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. By way of example, if untreated soybeans yielded 35 bu/ac, and if soybeans that received the subject treatment yielded 38 bu/ac under the same growing conditions, then the yield of soybeans would be said to have been increased by $((38-35)/35) \times 100 = 8.5\%$.

When the subject method is described herein as "increasing the vigor" of an agronomic plant, what is meant is that the vigor rating, or the plant weight, or the plant height, or the plant canopy, or the visual appearance, or any combination of these factors, is increased or improved by a measurable or noticeable amount over the same factor of the plant produced under the same conditions, but without the application of the subject method. It is preferred that such factor(s) is increased or improved by a significant amount.

As used herein the terms "fungal pest pressure", or "pest pressure by fungal plant pathogen", mean harm or damage to the plant or to its propagation material that is caused by fungal pathogens of the plant. Harm or damage is considered to be any such harm or damage that would normally be recognized as such by a skilled practitioner in the field of agriculture and farming. The terms "absence of pest pressure", or "lack of pest pressure", refer to the case where any harm or damage that is caused to the plant or its propagation material by the pest being described is either nonexistent, or is so minor that it would not normally be considered to be harm or damage by the skilled practitioner. In a preferred embodiment, a plant or seed that was sown, sprouted and/or grown in an environment having an absence of fungal pest pressure, or which was free of pest pressure due to fungal pathogens, would be rated as having the least, or lowest, amount of damage or harm due to fungal pests if analyzed by a test method wherein harm or damage to the plant or its propagation material is rated, by whatever scale that is used, from lowest to highest. One example of an environment that has an absence of fungal pest pressure is a sterile environment.

Although the novel method can be used with any agronomic plant, it is preferred that it be used with legumes (members of the class Magnoliopsida and the order Fabales). It is more preferred that the plant be in the family Fabaceae (formerly Leguminosae) and the sub-family Papilionoideae or Faboideae, and even more preferred that the plant be selected from the group consisting of *Pisum* spp. (including the garden pea, *P. sativum*), *Medicago* spp. (including alfalfa, *M. sativa*), *Arachis* spp. (including peanuts, *A. hypogaea*), soybeans (including *Glycine max, Glycine hispida*), *Vicia* spp. (including vetches), *Vigna* spp. (including cowpeans), *Vicia* spp. (including fava bean, *V. faba*), trefoil, clovers and *Phaseolus* spp. (including *P. vulgaris, P. lunatus, P. limensis*, and *P. coccineus*). It is most preferred that the present invention be used with soybeans.

It is believed that plants and plant propagation material that are suitable for use in the present invention can be non-transgenic plants, or can be plants that have at least one transgenic event. Transgenic events can include genetic material that is capable of encoding the production of pesticidal proteins. Examples of transgenic events that are useful in the present invention, seeds and plants that comprise such events, as well as examples of methods for their use, can be found in U.S. Pat. Nos. 6,313,378; 6,288,312; 6,284,949; 6,281,016; 6,242,241; 6,221,649; 6,218,145; 6,215,048; 6,211,430; 6,197,747; 6,177,615; 6,156,573; 6,153,814; 6,140,075; 6,114,610; 6,110,464; 6,107,549; 6,093,695; 6,084,161; 6,080,560; 6,063,756; 6,063,597; 6,037,527; 6,023,013; 6,018,100; 5,962,264; 5,959,091; 5,914,451; 5,898,096; 5,880,275; 5,869,720; 5,866,775; 5,859,347; 5,792,937; 5,773,701; 5,763,241; 5,759,538; 5,679,343; 5,633,435; 5,631,152; 5,627,061; 5,616,319; 5,593,874; 5,569,834; 5,500,365; 5,495,071; 5,463,175; 5,424,412; 5,378,619; 5,349,124; 5,312,910; 5,250,515; 5,229,112; 5,188,642; 5,145,783; and 4,940,835, among others.

In an embodiment of the present invention where the subject method includes treatment of the seed and/or the foliage of a plant with a herbicide or other pesticides, it is preferred that the plant be a transgenic plant having a transgenic event that confers resistance to the particular herbicide or other pesticide that is employed. When a herbicide such as glyphosate is included in the treatment, it is preferred that the transgenic plant or plant propagation material be one having a transgenic event that provides glyphosate resistance. Some examples of such preferred transgenic plants having transgenic events that confer glyphosate resistance are described in U.S. Pat. Nos. 5,914,451, 5,866,775, 5,804,425, 5,776,760, 5,633,435, 5,627,061, 5,463,175, 5,312,910, 5,310,667, 5,188,642, 5,145,783, 4,971,908 and 4,940,835. When the transgenic plant is a transgenic soybean plant, such plants having the characteristics of "Roundup-Ready" transgenic soybeans (available from Monsanto Company, St. Louis, Mo.) are preferred.

It is to be understood, however, that when the plant is a transgenic plant, the transgenic events that are present in the plant are by no means limited to those that provide herbicide or pesticide resistance, but can include any transgenic event. In fact, the use of "stacked" transgenic events in a plant is also contemplated.

The present invention is also useful for application to plants and propagation material which have been improved by a program of selective breeding based on quantitative trait loci (QTL) information. Further information about the use of such breeding programs can be found in U.S. Pat. No. 5,476,524, and in Edwards, M. D. et al., *Genetics*, 116: 113–125 (1987); Edwards, M. D. et al., *Theor. Appl. Genet.*, 83:765–774 (1992); Paterson, A. H. et al., *Nature*, 335: 721–726 (1988); and Lander, E. S. et al., *Mapping Medelian Factors Underlying Quantitative Traits Using RFLP Linkage Maps*, Genetics Society of America, pp. 185–199 (1989).

The present method is particularly useful for application to soybeans for which the yield has been improved through a QTL-directed selective breeding program.

The present method can be applied to any form of the plant that is to be treated, or any propagation material for the plant. For example, the method can be used to treat a plant seed at any time after its formation, or to treat the roots, leaves stems, shoots and/or fruit of the plant at any time after germination.

The active agents that are suitable for use in the present invention include certain chemical compounds that have demonstrated activity against plant pathogenic fungi, and in one embodiment, against *Gaeumannoyces graminis* microorganisms.

In a preferred embodiment, the active agent of the present invention is a diazole fungicide, a triazole fungicide, or a strobilurin-type fungicide, or a combination of any two or more of these fungicides with others of these types, or with certain fungicides of different types. Generally, when a diazole, triazole, or strobilurin-type fungicide is used, any diazole fungicide, triazole fungicide, or strobilurin-type fungicide can serve as the preferred fungicide in the present method or composition. Examples of diazole fungicides, triazole fungicides and strobilurin-type fungicides are identified in *The Pesticide Manual*, 12$^{th}$ Ed., C. D. S. Tomlin, Ed., British Crop Protection Council, Farnham, Surrey, UK (2000), but such listing is not intended to be limiting.

It is preferred that the active agent is a fungicide that is systemic in the agronomic plant or seed that is treated. When the fungicide is described as being "systemic", it is meant that the fungicide is absorbed into the seed and/or plant tissues and transported, at least to some degree, throughout all or some parts of the plant.

It is also preferred that the active agent is a fungicide having low phytotoxicity against the seed and/or plant that is treated. When it is said that the fungicide has low phytotoxicity, it is meant that the amount of the fungicide that is required to increase the vigor and/or the yield of the plant is insufficient to cause damage to the seed or to the plant at levels that counterbalance or overwhelm the beneficial activity of the active agent. It is more preferred that the fungicide, when applied in an efficacious amount, causes damage that is insignificant. It is even more preferred that the fungicide, when applied in an efficacious amount, causes no measurable damage.

Examples of triazole fungicides that are preferred for use in the present invention include, without limitation, amitrol, azaconazole, bitertanol, bromuconazole, climbazole, clotrimazole, cyproconazole, diclobutrazol, difenoconazole, diniconazole, diniconazole-M, epoxiconazole, etaconazole, fenbuconazole, fluquinconazole, fluotrimazole, flusilazole, flutriafol, furconazole, furconazole-cis, hexaconazole, imibenconazole, ipconazole, metconazole, myclobutanil, paclobutrazol, penconazole, propiconazole, quinconazole, simeconazole, tebuconazole, tetraconazole, triadimefon, triadimenol, triazbutil, triticonazole, and 1-(4-fluorophenyl)-2-(1H-1,2,4-triazole-1-yl)ethanone. Mixtures of such triazoles can also be used.

Diazole fungicides that are useful in the present invention include imidazoles and pyrazoles. Examples of diazole fungicides that are useful include, without limitation, imazalil, oxpoconazole, pefurazoate, prochloraz, and trifulmizole. Mixtures of such diazoles can also be used.

Examples of strobilurin-type fungicides that are useful in the present invention include, without limitation, azoxystrobin, dimoxystrobin, famoxadone, kresoxim-methyl, metominostrobin, picoxystrobin, pyraclostrobin, and trifloxystrobin. Mixtures of strobilurin type fungicides can also be used.

It is also believed that mixtures that include one or more diazole fungicide, one or more tiazole fungicide, and/or one or more strobilurin-type fungicide can also be used.

Other triazole fungicides that are useful in the present composition are those that are described in U.S. Pat. Nos. 4,510,136; 5,489,606; and 5,977,152.

Compounds that are preferred for use as the triazole fungicide are described in European Patent EP 0 609 099 A1 and U.S. Pat. No. 5,306,712. Such compounds have the formula:

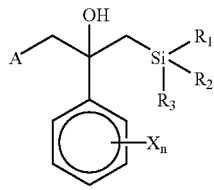

wherein:

A is a 1,2,4-triazol-1-yl group or an imidazol-1-yl-group;

n is 0, 1, 2, or 3, and when n is 2 or 3, the groups represented by X may be the same or different;

X is a halogen atom, a phenyl group, an alkyl group having from 1 to 6 carbon atoms, a haloalkyl group having from 1 to 6 carbon atoms and having at least one halogen atom, an alkoxy group having from 1 to 6 carbon atoms, or a haloalkoxy group having from 1 to 6 carbon atoms and having at least one halogen atom, or $(X)_n$ is an alkylenedioxy group having 1 or 2 carbon atoms;

$R_1$ is an alkyl group having from 1 to 4 carbon atoms or a phenyl group which is unsubstituted or is substituted by at least one halogen atom; and $R_2$ and $R_3$ are the same or different and each is an alkyl group having from 1 to 4 carbon atoms;

or a salt thereof.

Simeconazole ((RS)-2-(4-fluorophenyl)-1-(1H-1,2,4-triazol-1-yl)-3-(trimethylsilyl)propan-2-ol, Reg. No. 149508-90-7), is a preferred compound of this type of fungicide.

Other compounds that are preferred for use as the fungicide of the present combination are fungicidal imidazoles and 1,2,4-triazoles that are described in GB Patent 1 533 706, and having the general formula:

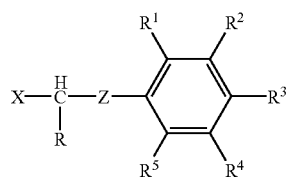

wherein R is hydrogen or an optionally substituted hydrocarbyl group, Z is

or a functional derivative thereof, each of the groups $R^1$ to $R^5$, which may be the same or different, in a hydrogen or halogen atom, an optionally substituted hydrocarbyl or hydrocarbyloxy group, or a nitro or amino group, and X is a group of general formula (A), (A') or (B);

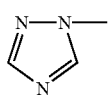 (A)

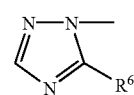 (A')

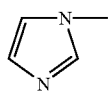 (B)

wherein $R^6$ is a halogen atom or an alkyl group;

R being an optionally substituted hydrocarbyl group other than an alkyl group when X is a group of general formula (B);

or a salt thereof.

A preferred triazole fungicide is simeconazole, which has a CAS name of α-(4-fluorophenyl)-α-[(trimethylsilyl)methyl]-1H-1,2,4-triazole-1-ethanol, and a CAS Reg. No. of 149508-90-7. A commercial preparation containing simeconazole is available, for example, as Simeconazole F-155, from Sankyo.

Another preferred triazole fungicide is 1-(4-fluorophenyl)-2-(1H-1,2,4-triazole-1-yl)ethanone, having the formula:

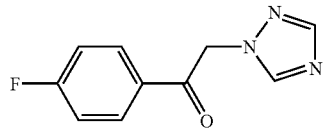

Another preferred triazole fungicide is fluquinconazole, having CAS Reg. No. 136426-54-5, and having a CAS chemical name of 3-(2,4-dichlorophenyl)-6-fluoro-2-(1H-1,2,4-triazol-1-yl)-4(3H)-quinazolinone.

Such preferred triazole fungicides share the structural features of a halogen-substituted phenyl group that is linked to a 1,2,4-triazole group. Without being bound to this or any other theory, the inventors believe that a triazole fungicide having these structural features may provide a composition having unexpectedly superior yield and/or vigor improvement properties.

Examples of triazole fungicides that are preferred for use in the present invention include fluquinconazole, simeconazole, tebuconazole, tetraconazole, triticonazole, and 1-(4-fluorophenyl)-2-(1H-1,2,4-triazol-1-yl)ethanone, or mixtures thereof.

In other embodiments of the invention, certain combinations of fungicides are preferred. Among such preferred combinations are: a combination of fluquinconazole and simeconazole; a combination of simeconazole and azoxystrobin; a combination of fluqinconazole and azoxystrobin; and a combination of any diazole, triazole and/or strobilurin-type fungicide with a silthiofam-type fungicide.

Silthiofam-type fungicides are described, for example, in U.S. Pat. Nos. 5,482,974, 5,486,621, 5,498,630, 5,693,667, 5,693,667, 5,705,513, 5,811,411, 5,834,447, 5,849,723, 5,994,270, 5,998,466, 6,028,101, and in publications WO 93/07751, and EP 0 538 231 A1. In particular, such compounds are described in WO 93/07751 and in European Patent Application No. 0 538 231 A1, which describe compounds having the general formula (I), below:

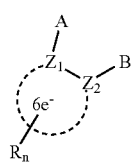

(I)

wherein $Z_1$ and $Z_2$ are C or N and are part of an aromatic ring selected from benzene, pyridine, thiophene, furan, pyrrole, pyrazole, thiazole, and isothiazole;

A is selected from —C(X)-amine, —C(O)—SR$_3$, —NH—C(X)R$_4$, and —C(=NR$_3$)—XR$_7$;

B is —W$_m$-Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino;

wherein two R$_2$ groups may be combined to form a cyclo group with Q;

R$_3$ is $C_1$–$C_4$ alkyl;

R$_4$ is $C_1$–$C_4$ alkyl, haloalkyl, alkoxy, alkylthio, alkylamino, or dialkylamino;

R$_7$ is $C_1$–$C_4$ alkyl, haloalkyl, or phenyl, optionally substituted with halo, nitro, or R$_4$;

or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy: alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono-or dialkylamino; phenyl, phenylalkyl or phenylalkenyl, each optionally substituted with one or more $C_1$–$C_6$ alkyl, alkoxy, haloalkyl, $C_3$–$C_6$ cycloalkyl, halo, or nitro groups; $C_1$–$C_4$ alkyl or alkenyl groups substituted with heterocycles, optionally substituted with one or more $C_1$–$C_4$ alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more $C_1$–$C_6$ alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl)oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6,6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino. Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyldimethylsilyl, hexyldimethylsilyl, cyclopropyldimethylsilyl, cyclobutyldimethylsilyl, cyclopentyldimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula $Si(R_2)_3$; any such silyl group connected to the $Z_1$–$Z_2$ ring by a methylene group; and any of these groups wherein germanium or tin is substituted for silicon. Of these examples of B, trimethylsilyl is preferred.

Further examples of B include 1,1-dimethylethyl, 1,1-dimethylpropyl, 1,1-dimethylbutyl, 1,1-dimethylpentyl,1-ethyl-1-methylbutyl, 2,2-dimethylpropyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propynyl, 1,1-dimethyl-2-butynyl, 1-cyclopropyl-1-methylethyl, 1-cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino)ethyl, 1,1-dimethyl-2-(dimethylamino)ethyl, 1,1-dimethyl-3-chloro-2-propenyl, 1-methyl-1-methoxyethyl, 1-methyl-1-(methylthio)ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylethyl is preferred.

Further examples of B are 1,1-dimethylethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-1-methylethylamino, 1-cyclopentyl-1-methylethylamino, 1-(1-cyclopentenyl)-1-methylethylamino, 1-cyclohexyl-1-methylethylamino, 1-(1-cyclohexenyl)-1-methylethylamino, 1-methyl-1phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)ethylamino, 1,1-dimethyl-2-(dimethylamino)ethylamino, and 1,1-dimethyl-3-chloro-2-propenylamino. Any of these groups may also have a methyl substitution on the nitrogen, as in N-(methyl)-1,1-dimethylethylamino and N-(methyl)-1,1-dimethylpropylamino. Of these examples of B, 1,1-dimethylethylamino and N-(methyl)-1,1-dimethylethylamino are preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1-cyclohexenyl)-1-methylethoxy, 1-methyl-1-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylethoxy is preferred.

Further examples of B include methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, 1-methylcyclohexylamino, N-(methyl)-1-methylcyclopropylamino, N-(methyl)-1-methylcyclobutylamino, N-(methyl)-1-methylcyclopentylamino, and N-(methyl)-1-methylcyclohexylamino.

$R_n$ may be any substituent(s) which do(es) not unduly reduce the effectiveness of the compounds to function in the method of disease control. $R_n$ is generally a small group; "n" is preferably 1 for benzene rings and 2 for furan and thiophene. R is more preferably methyl or halogen, and more preferably is located adjacent to A.

As used herein, the term "alkyl", unless otherwise indicated, means an alkyl radical, straight or branched chain, having, unless otherwise indicated, from 1 to 10 carbon atoms. The terms "alkenyl" and "alkynyl" mean unsaturated radicals having from 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methylethenyl, and the like. Examples of such alkynyl groups include ethynyl, 1-propynyl, 2-propynyl, 1,1-dimethyl-2-propynyl, and so forth. Substituent groups may also be both alkenyl and alkynyl, for example, 6,6-dimethyl-2-hepten-4-ynyl.

As used herein, the term "alkoxy" means an alkyl group having, unless otherwise indicated, from 1 to 10 carbon atoms connected via an ether linkage. Examples of such alkoxy groups include methoxy, ethoxy, propoxy, 1-methylethoxy, and so forth.

As used herein, the term "alkoxyalkyl" means an ether radical having, unless otherwise indicated, from 1 to 10 carbon atoms. Examples of such alkoxyalkyl groups include methoxymethyl, methoxyethyl, ethoxymethyl, ethoxyethyl, and so forth.

As used herein, the terms "monoalkylamino" and "dialkylamino" each mean an amino group having, respectively, 1 or 2 hydrogens replaced with an alkyl group.

As used herein, the term "haloalkyl" means an alkyl radical having one or more hydrogen atoms replaced by halogens, including radicals having all hydrogen atoms substituted by halogen. Examples of such haloalkyl groups are fluoromethyl, difluoromethyl, trifluoromethyl, chloromethyl, trichloromethyl, and so forth.

As used herein, the term "halo" means a radical selected from chloro, bromo, fluoro, and iodo.

Silthiofam-type compounds that are useful in combinations of the present invention include compounds that are described in U.S. Pat. No. 5,811,411 as compounds having the same formula as in Formula (I), above, except:

wherein $Z_1$ and $Z_2$ are C and are part of an aromatic ring which is thiophene;

A is selected from —C(X)-amine, —C(O)—SR$_3$, —NH—C(X)R$_4$, and —C(=NR$_3$)—XR$_7$;

B is —W$_m$-Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) C$_1$–C$_4$ alkyl, alkenyl, alkynyl, C$_3$–C$_6$ cycloalkyl, and cycloalkenyl, each optionally substituted with halo, hydroxy, thio, amino, nitro, cyano, formyl, phenyl, C$_1$–C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, C$_1$–C$_4$ alkyl, alkenyl, alkynyl, alkoxy, alkylthio, alkylamino, dialkylamino, haloalkyl, and haloalkenyl;

d) C$_1$–C$_4$ alkoxy, alkenoxy, alkynoxy, C$_3$–C$_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino, and further when Q is C, R$_2$ may also be selected from halo, alkoxy, alkylthio, alkylamino, and dialkylamino; and further when Q is C, then two R$_2$ groups may be combined to form a cycloalkyl group with Q;

R$_3$ is C$_1$–C$_4$ alkyl;

R$_4$ is C$_1$–C$_4$ alkyl, haloalkyl, alkoxy, alkylthio, alkylamino, or dialkylamino;

R$_7$ is C$_1$–C$_4$ alkyl, haloalkyl, or phenyl, optionally substituted with halo, nitro, or R$_4$;

or an agronomic salt thereof.

Silthiofam-type fungicides that are useful in combinations of the present invention include compounds that are described in U.S. Pat. No. 5,998,466 as compounds having the same formula as in Formula (I), above, except:

wherein Z$_1$ and Z$_2$ are C and are part of an aromatic ring which is thiophene;

A is selected from —C(X)-amine, wherein the amine is substituted with a first and a second amine substituent or with an alkylaminocarbonyl and a hydrogen, —C(O)—SR$_3$, —NH—C(X)R$_4$, and —C(=NR$_3$)—XR$_7$;

the first amine substituent is selected from the group consisting of C$_1$–C$_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, C$_3$–C$_6$ cycloalkyl and C$_5$–C$_6$ cycloalkylkenyl; phenyl optionally substituted with one or more C$_1$–C$_4$ straight or branched alkyl, alkenyl, or alkynyl groups or mixtures thereof, cycloalkyl, cycloalkenyl, haloalkyl, alkoxy and nitro; C$_3$–C$_6$ cycloalkyl, C$_5$–C$_6$ cycloalkenyl, alkoxy, alkenoxy, alkynoxy, dialkylamino, and alkylthio;

and the second amine substituent is selected from the group consisting of hydrogen; C$_1$–C$_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —W$_m$-Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$— and —O—;

X is O or S;

n is 2;

m is 0 or 1;

p is 0, 1, or 2;

wherein two R groups are combined to form a nonheterocyclic ring fused with the thiophene ring, which is not a benzothiophene other than a tetrahydrobenzothiophene, said two R groups being selected from the group consisting of C$_1$–C$_4$ alkyl, alkenyl, C$_3$–C$_6$ cycloalkyl and cycloalkenyl, each optionally substituted with hydroxy, thio, phenyl, C$_1$–C$_4$ alkoxy, alkylthio, alkylsulfinyl, or alkylsufonyl;

each R$_2$ is independently selected from alkyl, alkenyl, alkynyl, cycloalkyl, cycloalkenyl and phenyl, each optionally substituted with R$_4$ or halogen; and wherein when Q is C, R$_2$ may also be selected from halo, alkoxy, alkylthio, alkylamino, and dialkylamino; and further when Q is C, then two R$_2$ groups may be combined to form a cycloalkyl group with Q;

R$_3$ is C$_1$–C$_4$ alkyl;

R$_4$ is C$_1$–C$_4$ alkyl, haloalkyl, alkoxy, alkylthio, alkylamino, or dialkylamino; and R$_7$ is C$_1$–C$_4$ alkyl, haloalkyl, or phenyl, optionally substituted with halo, nitro, or R$_4$;

or an agronomic salt thereof.

Silthiofam-type fungicides that are useful in combinations of the present invention include compounds that are described in U.S. Pat. No. 5,834,447 as compounds having the same formula as in Formula (I), above, except:

wherein Z$_1$ and Z$_2$ are C and are part of an aromatic ring which is thiophene;

A is —C(X)-amine wherein the amine is an N-bonded heterocyclic compound chosen from the group consisting of morpholine, piperazine, piperidine, and pyrrolidine, each optionally substituted with C$_3$–C$_6$ alkyl groups;

B is —W$_m$-Q(R$_2$)$_3$ or selected from o-tolyl, 1-naphthyl, 2-naphthyl, and 9-phenanthryl, each optionally substituted with halogen or R$_4$;

Q is C or Si;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O;

n is 2;

m is 0 or 1;

p is 0, 1, or 2;

wherein the two R groups are alkenyl groups and are combined to form a fused ring with the thiophene ring with is benzothiophene; wherein the alkenyl groups are optionally substituted with halo, hydroxy, thio, amino, nitro, cyano, formyl, phenyl, C$_2$–C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

each R$_2$ is independently selected from alkyl, alkenyl, alkynyl, cycloalkyl, cycloalkenyl, and phenyl, each optionally substituted with R$_4$ or halogen; and wherein when Q is C, R$_2$ may also be selected from halo, alkoxy, alkylthio, alkylamino, and dialkylamino; or wherein two $R_2$ groups may be combined to form a cyclo group with Q;

$R_3$ is $C_1$–$C_4$ alkyl; and $R_4$ is $C_1$–$C_4$ alkyl, haloalkyl, alkoxy, alkylthio, alkylamino, or dialkylamino;

or an agronomic salt thereof.

Silthiofam-type fungicides that are useful in combinations of the present invention include compounds that are described in U.S. Pat. No. 5,498,630 as compounds having the same formula as in Formula (I), above, except:

wherein $Z_1$ and $Z_2$ are C and are part of an aromatic ring which is benzothiophene; and A is selected from —C(X)-amine wherein the amine is an unsubstituted, monosubstituted or disubstituted nonheterocyclic amino radical, —C(O)—$SR_3$, —NH—C(X)$R_4$, and —C(=$NR_3$)—$XR_7$;

B is —$W_m$-Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention include compounds that are described in U.S. Pat. No. 5,693,667 as compounds having the same formula as in Formula (I), above, except:

wherein $Z_1$ and $Z_2$ are C or N and are part of an aromatic ring which is furan; and A is selected from —C(X)-amine wherein the amine is substituted with a first and a second amine substituent or with an alkylaminocarbonyl and a hydrogen, —C(O)—$SR_3$, —NH—C(X)$R_4$, and —C(=$NR_3$)—$XR_7$;

the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$–$C_6$ cycloalkyl and $C_5$–$C_6$ cycloalkylkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen; $C_1$–$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$-Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention include compounds that are described in U.S. Pat. No. 5,498,630 as compounds having the same formula as in Formula (I), above, except:

wherein $Z_1$ and $Z_2$ are C and are part of an aromatic ring which is benzothiophene; and A is selected from —C(X)-amine wherein the amine is an unsubstituted, monosubstituted or disubstituted nonheterocyclic amino radical, —C(O)—SR$_3$, —NH—C(X)R$_4$, and —C(=NR$_3$)—XR$_7$;

B is —W$_m$-Q(R$_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, 2, or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention include compounds that are described in U.S. Pat. No. 5,693,667 as compounds having the same formula as in Formula (I), above, except:

wherein $Z_1$ and $Z_2$ are C and are part of an aromatic ring which is furan; and A is selected from —C(X)-amine wherein the amine is substituted with a first and a second amine substituent or with an alkylaminocarbonyl and a hydrogen, —C(O)—SR$_3$, —NH—C(X)R$_4$, and —C(=NR$_3$)—XR$_7$;

the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$–$C_6$ cycloalkyl and $C_5$–$C_6$ cycloalkylkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen; $C_1$–$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —W$_m$-Q(R$_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

wherein two R groups may be combined to form a fused ring;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q which is 1-methylcyclopropyl, 1-methylcyclopentyl, or 1-methylcyclohexyl;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention include compounds that are described in U.S. Pat. No. 5,705,513 as compounds having the same formula as in Formula (I), above, except:

wherein $Z_1$ and $Z_2$ are C and are part of an aromatic ring which is pyridine; and A is selected from the group consisting of —C(O)—SR$_3$, —NH—C(X)R$_4$, and —C(=NR$_3$)—XR$_7$ and —C(X)-amine wherein the amine is substituted with alkylaminocarbonyl and a hydrogen or wherein the amine has a first and a second amine substituent;

the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$–$C_6$ cycloalkyl and $C_5$–$C_6$ cycloalkylkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen; $C_1$–$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —W$_m$-Q(R$_2$)$_3$ or selected from o-tolyl, 1-naphthyl, 2-naphthyl, and 9-phenanthryl, each optionally substituted with halogen or R$_4$;

Q is C, Si, Ge, or Sn;

W is —C(R$_3$)$_p$H$_{(2-p)}$—; or when Q is C, W is selected from —C(R$_3$)$_p$H$_{(2-p)}$—, —N(R$_3$)$_m$H$_{(1-m)}$—, —S(O)$_p$—, and —O—;

X is O or S;

n is 0, 1, or 2;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each R$_2$ is independently selected from alkyl, alkenyl, alkynyl, cycloalkyl, cycloalkenyl and phenyl, each optionally substituted with R$_4$ or halogen; and wherein, when Q is C, R$_2$ may also be selected from halo, alkoxy, alkylthio, alkylamino, and dialkylamino; or wherein two R$_2$ groups may be combined to form a cyclo group with Q which is 1-methylcyclopropyl, 1-methylcyclopentyl, or 1-methylcyclohexyl;

R$_3$ is $C_1$–$C_4$ alkyl;

R$_4$ is $C_1$–$C_4$ alkyl, haloalkyl, alkoxy, alkylthio, alkylamino, or dialkylamino; and R$_7$ is $C_1$–$C_4$ alkyl, haloalkyl, or phenyl, optionally substituted with halo, nitro, or R$_4$;

or an agronomic salt thereof.

Silthiofam-type fungicides that are useful in combinations of the present invention include compounds that are described in U.S. Pat. No. 5,849,723 as compounds having the same formula as in Formula (I), above, except:

wherein $Z_1$ and $Z_2$ are C and are part of an aromatic ring which is benzene; and A is selected from the group consisting of —C(X)-amine wherein the amine is substituted with a first and a second amine substituent or with an alkylaminocarbonyl and a hydrogen; —C(O)—SR$_3$, —NH—C(X)R$_4$, and —C(=NR$_3$)—XR$_7$;

the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, $C_3$–$C_6$ cycloalkyl and $C_5$–$C_6$ cycloalkylkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen; $C_1$–$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —W$_m$-Q(R$_2$)$_3$ or selected from o-tolyl, 1-naphthyl, 2-naphthyl, and 9-phenanthryl, each optionally substituted with halogen or R$_4$;

Q is Si, Ge, or Sn;

W is —C(R$_3$)$_p$H$_{(2-p)}$—;

X is O or S;

n is 0, 1, 2 or 3;

m is 0 or 1;

p is 0, 1, or 2;

each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each R$_2$ is independently selected from alkyl, alkenyl, alkynyl, cycloalkyl, cycloalkenyl and phenyl, each optionally substituted with R$_4$ or halogen;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention include compounds that are described in U.S. Pat. No. 6,028,101 as compounds having the same formula as in Formula (I), above, except:

wherein $Z_1$ and $Z_2$ are C and are part of an aromatic ring which is furan; and A is selected from —C(X)-amine wherein the amine is substituted with a first and a second amine substituent or with an alkylaminocarbonyl and a hydrogen, —C(O)—$SR_3$, —NH—C(X)$R_4$, and —C(=$NR_3$)—$XR_7$;

the first amine substituent is selected from the group consisting of $C_1$–$C_{10}$ straight or branched alkyl, alkenyl, or alkynyl groups or mixtures thereof optionally substituted with one or more halogen, hydroxy, alkoxy, alkylthio, nitrile, alkylsulfonate, haloalkylsulfonate, phenyl, a 5-membered heteroaryl, $C_3$–$C_6$ cycloalkyl and $C_5$–$C_6$ cycloalkylkenyl; phenyl optionally substituted with one or more $C_1$–$C_4$ straight or branched alkyl, alkenyl, or alkynyl groups or mixtures thereof, cycloalkyl, cycloalkenyl, haloalkyl, alkoxy and nitro; $C_3$–$C_6$ cycloalkyl, $C_5$–$C_6$ cycloalkenyl, alkoxy, alkenoxy, alkynoxy, dialkylamino, and alkylthio;

and the second amine substituent is selected from the group consisting of hydrogen; $C_1$–$C_6$ straight or branched alkyl, alkenyl, or alkynyl groups or mixtures thereof optionally substituted with one or more halogen, hydroxy, alkylcarbonyl, haloalkylcarbonyl, alkoxycarbonyl, and dialkylphosphonyl;

B is —$W_m$-Q($R_2$)$_3$ or selected from o-tolyl, 1-naphthyl, 2-naphthyl, and 9-phenanthryl, each optionally substituted with halogen or $R_4$;

Q is C, Si, Ge, or Sn;

W is —C($R_3$)$_p$H$_{(2-p)}$—; or when Q is C, W is selected from —C($R_3$)$_p$H$_{(2-p)}$—, —N($R_3$)$_m$H$_{(1-m)}$—, —S(O)$_p$—, and —O—;

X is O or S;

n is 2;

m is 0 or 1;

p is 0, 1, or 2;

wherein the two R groups are combined to form a nonheterocyclic ring fused to said furan ring which is not benzofuran when A is —C(X)-amine, B is —Wm(Q)—($R_2$)$_3$, and Q is C or Si, said R groups being selected from the group consisting of $C_1$–$C_4$ alkyl, alkenyl, $C_3$–$C_6$ cycloalkyl and cycloalkenyl, each optionally substituted with hydroxy, thio, phenyl, $C_1$–$C_4$ alkoxy, alkylthio, alkylsulfinyl, or alkylsulfonyl; and each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; wherein further when Q is C, then two $R_2$ groups may be combined to form a cyclo group with Q;

$R_3$ is $C_1$–$C_4$ alkyl;

$R_4$ is $C_1$–$C_4$ alkyl, haloalkyl, alkoxy, alkylthio, alkylamino, or dialkylamino; and $R_7$ is $C_1$–$C_4$ alkyl, haloalkyl, or phenyl, optionally substituted with halo, nitro, or $R_4$;

or an agronomic salt thereof.

Silthiofam-type fungicides that are useful in combinations of the present invention can also be selected from those described in U.S. Pat. No. 5,482,974, namely, a compound having the formula

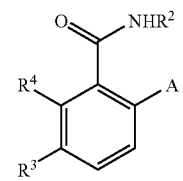

wherein $R^2$ is ethyl, iso-propyl, propyl or allyl;

A is N(CH$_3$)$_{1-n}$H$_n$R$^5$ or OR$^6$ wherein n is 0 or 1, R$^5$ is (CH$_3$)$_m$(CH$_3$CH$_2$)$_{3-m}$C, 1-methyl-1-cyclopentyl, 1-methyl-1-cyclohexyl or 2,3-dimethyl-2-butyl wherein m is 0, 1, 2 or 3 and R$^6$ is independently R$^5$, or 2,3,3-trimethyl-2-butyl;

R$^3$ is H or independently R$^4$; and

R$^4$ is halo or CH$_3$;

with the proviso that when A is N(CH$_3$)$_{1-n}$H$_n$R$^5$, if R$^3$ is H and R$^5$ is 1-methyl-1-cyclohexyl or (CH$_3$)$_m$(CH$_2$CH$_3$)$_{3-m}$C, where m is 0 or 3, or if R$^3$ is halo and R$^2$ is (CH$_3$)$_m$(CH$_3$CH$_2$)$_{3-m}$C, where m is 3, then R$^2$ cannot be ethyl;

and with the proviso that when A is OR$^6$ then m is equal to or less than 2, and if R$^3$ is H or halo and R$^2$ is ethyl or isopropyl, then R$^6$ is (CH$_3$)$_M$(CH$_3$CH$_2$)$_{3-M}$C where m is 1;

or an agronomic salt thereof.

Silthiofam-type fungicides that are useful in combinations of the present invention can also be selected from those described in U.S. Pat. No. 5,994,270, namely, a compound having the formula:

(a)
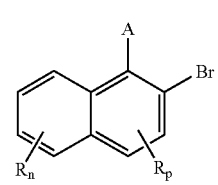

(b)
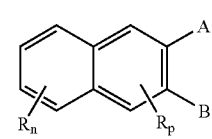

(c)
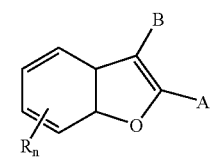

(d)
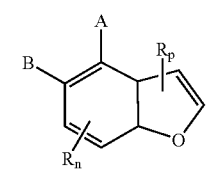

-continued (e)
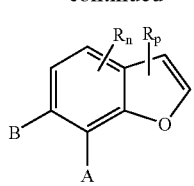

(f)
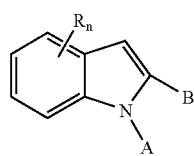

(g)
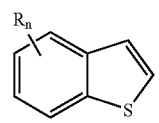

(h)
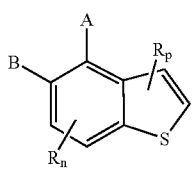

(i)
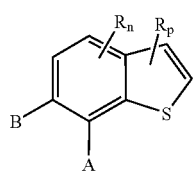

(j)
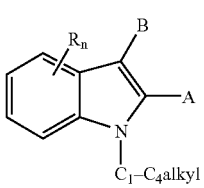

where A is —C(X)-amine; B is —$W_m$-Q($R_2$)$_3$; and A can be B when B is A except when the formula is f), then Q cannot be Si;

Q is C or Si;

W is —NH—, —O— or NCH$_3$—;

X is O or S;

m is 0 or 1, provided that m is 0 when Q is Si;

n is 0 1, 2, or 3;

p is 0, 1 or 2, and n plus p is equal to or less than 3; each R is independently selected from a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo; each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; wherein two $R_2$ groups may be combined to form a cyclo group with Q; $R_4$ is $C_1$–$C_4$ alkyl, haloalkyl, alkoxy, alkylthio, alkylamino, or dialkylamino; or an agronomic salt thereof.

A preferred silthiofam-type fungicide is a compound having the structure:

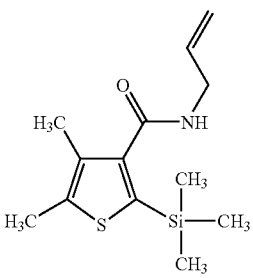

and which has a CAS name of 4,5-dimethyl-N-(2-propenyl)-2-(trimethylsilyl)-3-thiophenecarboxamide, having a CAS registration number of 175217-20-6, and for which the ISO common name is silthiofam. Further information about silthiofam can be found in U.S. Pat. No. 5,486,621.

Any of the fungicides that are useful in the present invention can be used in any purity that passes for such fungicide in the commercial trade. The fungicide can be used in any form in which it is received from the supplier, or in which it is synthesized. It is preferred that the fungicide be supplied in the form of a liquid, which form includes, without limitations, solutions, suspensions and dispersions. However, the liquid can be a substantially pure form of the fungicide, or it can be the fungicide dissolved in a solvent. Commonly, if a solvent is present, such solvents are organic liquid solvents that are commonly used in such applications. If the fungicide is water soluble, then water can be used as the solvent.

The treatment of a plant or its propagation material, such as a seed, with an active agent by the method of this invention can be accomplished in several ways. The agent may be applied directly to the seed and/or to soil in which the seed is to be planted, for example, at the time of planting along with the seed. Alternatively, it may be applied to the soil after planting and germination, or to the foliage of the plant after emergence. It is preferred that the active agent is applied directly to the seed prior to the seed being planted.

When it is said that "an effective amount" of a fungicide or other active agent is used in the subject method, it is meant that a sufficient amount of the fungicide or other active agent is applied to the plant or its propagation material to achieve an increase in the yield and/or the vigor of the plant. The amount of the active agents that are useful in the subject method will be discussed in more detail below.

Compositions for soil application include clay granules which may be applied in-furrow, as broadcast granules or as impregnated fertilizer granules. In addition, the agent may be applied to the soil as a preemergent or postemergent spray, or to the plant as a postemergent spray.

In one embodiment, the agent is applied to the seed in a treatment prior to planting. One method of carrying out such treatment is to apply a coating containing the active agent to the seed. This technique is commonly used in many crops to provide fungicides for control of various phytopathological fungi.

When the seed is treated prior to planting with a composition that contains the active agent, it can be treated with an amount of the composition sufficient to include the active agent, or total amount of active agents if a combination of two or more active agents is used, in an amount that is within the range of about 0.1 gm/1 00 kg of seed to about 1000 gm/100 kg of seed. It is preferred that the active agent be applied to the seed in an amount that is within the range of about 2 gm/100 kg and about 200 gm/100 kg, more preferred that it be applied in an amount of from about 10 gm/100 kg of seed to about 150 gm/100 kg of seed, and a range of about 20 gm/100 kg to about 100 gm/100 kg of seed is yet more preferred.

Plants and/or seed to be treated by the subject method can be treated with one or more forms of the useful active agents without any additional materials being present. However, in some cases, it is preferred to use the one or more active agents in combination with other materials in a composition.

Compositions of the present invention are comprised of an effective amount of one or more of the active agents described above and one or more adjuvants. If desirable, such compositions can also include such other materials as herbicides, pesticides—such as insecticides, nematicides, acaricides, fungicides, and the like, growth factors, fertilizers, and any other material that will provide a desirable feature for protecting, sprouting and growing the plant, and/or for improving the yield or vigor of the plant. The choice of such other materials will depend on the crop and the diseases known to be a threat to that crop in the location of interest. In one embodiment, the active agent can be combined with a herbicide for foliar application to the plant. Any of the active agents discussed above can be used in this combination.

When a herbicide is used with the active agent, any herbicide can be used, provided that the plant that is to be treated has resistance to such herbicide. As described above, it is preferred that the plant have a transgenic event providing the plant with resistance to the herbicide being used. Within these limitations, any herbicide can be used in the combination and useful herbicides include, without limitation, imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 00 H, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chloramben, chlorbromuron, chloridazon, chlorimuron-ethyl, chloroacetic acid, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D, daimuron, dalapon, dazomet, 2,4DB, desmedipham, desmetryn, dicamba, dichlobenil, dichlorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethalfluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, glufosinate, glufosinate-ammonium, glyphosate, glyfosinate, halosulfuron-methyl, haloxyfop, HC-252, hexazinone, imazamethabenz-methyl, imazamox, imazapyr, imazaquin, imazethapyr, imazosuluron, imidazilinone, indanofan, ioxynil, isoproturon, isouron, isoxaben, isoxaflutole, lactofen, lenacil, linuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachlor, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichloride, pebulate, pendimethalin, pentachlorophenol, pentanochlor, pentoxazone, petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, trietazine, trifluralin, triflusulfuron-methyl, and vernolate.

Preferred herbicides include glyphosate, glufosinate, glyfosinate, imidazilinone, and STS system (sulfonylurea).

When the active agent is a diazole, triazole, or strobilurin-type fungicide, a preferred herbicide is glyphosate, (N-(phosphonomethyl)glycine).

The active agent can be combined with a fungicide that is commonly used to treat seed or for foliar application to the particular plant that is of interest. In other words, it can be used along with a fungicide that is applied for its fungicidal properties, unlike the reason for applying the active agent of the present invention. For example, when the agronomic plant is soybeans, other fungicides, such as metalaxyl, carboxin, captan and thiram, which are active against the known soybean disease-causing organisms, can also be used along with the novel treatment. As an alternative, common fungicides such as captan, metalaxyl, carboxin and thiram can be used as a seed treatment, while the fungicide of the novel treatment method can be applied to the seed, the soil, or to the shoots and foliage of the plant itself.

It is also contemplated that the subject method can include treatment of a seed with an inoculant, followed by foliar treatment with an active agent, or by foliar treatment with an active agent and a herbicide. The subject treatment can also include the treatment of a seed with an inoculant and an active agent, followed by foliar treatment with an active agent and/or a herbicide. In any one of these treatment protocols, other fungicides and/or pesticides can be included at any step of the treatment method.

The active agent may be present in such compositions at levels from 0.01 to 95 percent by weight. Preferably, such compositions contain the active agent in an amount of from about 1% to about 50%, by weight, and more preferably, in an amount of from about 5% to about 25%, by weight.

The compositions of this invention, including concentrates that require dilution prior to application, may contain at least one active agent and an adjuvant in liquid or solid form. The compositions are prepared by admixing the active agent with or without an adjuvant plus diluents, extenders, carriers, and conditioning agents to provide compositions in the form of finely-divided particulate solids, granules, pellets, solutions, dispersions or emulsions. Thus, it is believed the active agent could be used with an adjuvant such as a finely-divided solid, a liquid of organic origin, water, a wetting agent, a dispersing agent, an emulsifying agent or any suitable combination of these.

Agronomically acceptable carriers for active agents are well known and include, for example, solid carriers such as fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. Acceptable liquid carriers include, for example, aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cottonseed oil, corn oil and the like, dimethyl sulfoxide, acetonitrile, water and the like.

Suitable wetting agents are believed to include alkyl benzene and alkyl naphthalene sulfonates, alkyl and alkyl aryl sulfonates, alkyl amine oxides, alkyl and alkyl aryl phosphate esters, organosilicones, fluoro-organic wetting agents, alcohol ethoxylates, alkoxylated amines, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, block copolymers, polyoxyalkylene derivatives of alkylphenols (particularly isooctylphenol and nonylphenol) and polyoxyalkylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, polymethylene bisnaphthalene sulfonate, and neutralized polyoxyethylated derivatives or ring-substituted alkyl phenol phosphates. Stabilizers may also be used to produce stable emulsions, such as magnesium aluminum silicate and xanthan gum.

Other formulations include dust concentrates comprising from 0.1 to 60% by weight of the active agent on a suitable extender, optionally including other adjuvants to improve handling properties, e.g., graphite. These dusts may be diluted for application at concentrations within the range of from about 0.1–10% by weight.

Concentrates may also be aqueous emulsions, prepared by stirring a non-aqueous solution of a water insoluble active agent and an emulsification agent with water until uniform and then homogenizing to give stable emulsion of very finely divided particles. Or they may be aqueous suspensions, prepared by milling a mixture of a water-insoluble active agent and wetting agents to give a suspension, characterized by its extremely small particle size, so that when diluted, coverage is very uniform. Suitable concentrations of these formulations contain from about 0.1–60% preferably 5–50% by weight of active agent.

Concentrates may be solutions of active agent in suitable solvents together with a surface active agent. Suitable solvents for the active agents of this invention for use in seed treatment include propylene glycol, furfuryl alcohol, other alcohols or glycols, and other solvents that do not substantially interfere with seed germination. If the active agent is to be applied to the soil, then solvents such as N,N-dimethylformamide, dimethylsulfoxide, N-methylpyrrolidone, hydrocarbons, and water immiscible ethers, esters, or ketones are useful.

The concentrate compositions herein generally contain from about 1.0 to 95 parts (preferably 5–60 parts) of the active agent, about 0.25 to 50 parts (preferably 1–25 parts) surface active agent and where required about 4 to 94 parts solvent, all parts being by weight based on the total weight of the concentrate.

An example of a formulation that is useful for seed treatment includes a diazole, triazole, or strobilurin-type fungicide, preferably at a concentration of about 10%; a dispersant, preferably at a concentration of about 3%; a phosphate buffer, preferably comprising sodium and potassium phosphate in a ratio to provide buffering at a pH that is within a range of from about 5 to about 9, and preferably in an amount of about 1.5%; one or more crystal growth inhibitors, preferably in an amount of about 2.4%; an antifoam agent, preferably in an amount of about 0.1%; a surfactant, preferably in an amount of about 0.5%; a colorant, preferably in an amount of about 8%; a polymer sticker or binder, preferably in an amount of about 7%; a thickener, preferably in an amount of about 0.1%; glycerin, preferably in an amount of about 5%; and with the remainder being water; where all concentrations are given on a weight basis.

For application to the soil at the time of planting, a granular formulation may be used. Granules are physically stable particulate compositions comprising at least one active agent adhered to or distributed through a basic matrix of an inert, finely divided particulate extender. In order to aid leaching of the active agent from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely divided clays such as kaolin clays, hydrated attapulgite or bentonitic clays. These extenders are sprayed or blended with the active agent to form the granules.

The granular compositions of this invention may contain from about 0.1 to about 30 parts by weight of active agent per 100 parts by weight of clay and 0 to about 5 parts by weight of surface active agent per 100 parts by weight of particulate clay.

The method of the present invention may be carried out by mixing the composition comprising the active agent into the seed prior to planting at rates that have been described above. If application to the soil is desired, the compounds may be applied at any rate that will provide an effective amount. However, rates from 1 to 1000 g per hectare are preferred, and from 10 to 500 g per hectare are more preferred. The higher application rates is believed to be needed for situations of light soils or greater rainfall or both.

When the active agent is used to treat seeds, it is preferred that an inoculant be used. The inoculant can be any one of the types of inoculant that is known for use with the type of plant that is the subject of treatment. For example, if corn is being treated, the corn seed could be treated with an inoculant containing *Azospirillium* spp. When a legume is being treated, the inoculant can be one that is known for use with legumes. Some examples of inoculants that are used in the culture of legumes are those including *Rhizobium* spp., a *Bradyrhizobium* spp., or a mixture thereof, or a mixture of either of those bacterium with one or more other microorganism strains. Examples of useful inoculants include a *Bradyrhizobium japonicum* inoculant (USDA Soybean Inoculant) produced by Urbana Laboratories of Urbana, Ill.

If an inoculant is used, it can be applied at any time, and at any rate, and by the use of any method of application. When the inoculant is to be used in conjunction with seed that has been treated with the subject active agent, it is preferred that the treated seed be contacted with the inoculant before planting. It is more preferred that the treated seed be contacted with the inoculant within a time before planting that is sufficiently brief so as to minimize any negative effect that the active agent might have on the inoculant. The inoculant can be applied to the treated seeds no more than 24 hours before planting, preferably no more than 10 hours before planting, and more preferably no more than 5 hours before planting.

Alternatively, the inoculant can be applied to the soil surrounding the seed at the time of planting, or it may be administered to the soil at any time after planting. One method of applying the active agent to the soil surrounding the seed at the time of planting is to add the inoculant to the seed furrow at the same time the seed is planted. Any of these methods should be considered to be included when it is mentioned herein that seed is treated with an inoculant.

Although any amount of the inoculant can be added to the seed, it is preferred that the inoculant be added at approximately the rate recommended by its supplier. When the inoculant is provided in the form of a culture of bacterium that is distributed on peat or humus, for example, the inoculant can be applied to the seed at a rate of from about 1 g/kg of seed to about 50 g/kg of seed, and preferably at a rate of about 10 g/kg of seed.

When an inoculant is contacted with seed, a sticking agent can also be used to help to adhere an even coating of the inoculant to each seed. Many such sticking agents are known in the art and any can be used. When a sticking agent is used, it can be used at any rate, but it is preferred that it is used at the rate that is recommended by its supplier. By way of example, it is preferred that the sticking agent is applied to the seed prior to the application of the inoculant at a rate of from about 40 ml/100 kg of seed to about 4,000 ml/100 kg of seed, more preferably at a rate of about 400 ml/100kg of seed.

The active agents of the present invention can also be applied to seed or to soil in the form of controlled release formulations. Such controlled release formulations are well known in the art and include microparticles, microcapsules, matrix coatings, matrix granules, and the like.

As mentioned above, it is believed that the present invention is particularly advantageous when applied to plants or seeds that are, or will become, under some type of stress prior to, during, or after germination. Drought, excessive cold or heat, combinations of cold and wet conditions, and other such conditions commonly cause such stress. Such stress can also be affected by unsuitable nutritional or ionic conditions of the soil, and the like. Accordingly, it is believed that the subject method would be particularly useful for such farming practices as dry-land farming, no-till farming, use of conservative farming practices, early planting, or any other technique or situation which could cause stress on the seeds and/or the plants.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This example illustrates the preparation of a seed treatment formulation that includes simeconazole.

Glycerin (6.82 g) was mixed in a beaker with a spatula with Lomar D (3.81 g, Lot 7H8966, Sample No. RM2527, available from Henkel) to form a paste. Deionized water (28.0 g) was added to the paste with stirring to form a homogeneous solution. A phosphate buffer solution (1.8 g; Sample No. RM3580, Lot No. SFD66D, available from Monsanto Europe, Antwerp, Belgium) was added to the solution with stirring to bring the pH to 7.1.

Simeconazole (12.0 g, prepared according to the method described by Itoh, H. et al., in *Chemical and Pharmaceutical Bulletin,* 8:1148–1153 (2000), or in European Patent Application No. 0 609 099 A1) was added to the solution with stirring, as was Aerosil R972 (0.28 g, available from Degussa) and Hostapon (0.56 g, N-methyl-N-oleyl(tauride), Lot No. 10113264, available from Hoechst Ag). The mixture was stirred with a spatula and the larger solid particles were crushed. Agsolex 8 (0.11 g, available from International Specialty Products) was added to the suspension, and the suspension was mixed using a high shear mixer (Silverson) at 9900 rpm for 30 seconds.

An antifoam agent (0.12 g, Rhodorsil 432, available from Rhodia) was added to collapse the foam that had formed in the mixture. Orchex 796 (2.27 g, available from Exxon) was added and the high shear mixer was again used to mix the solution for 30 seconds. Deionized water (11.0 g) was added to the slurry with stirring. At this point, the total amount of the mixture was 66.5 g.

The mixture was added to a mini Eiger mill (available from Eiger Machinery Inc., model MK11 M50) and mixed at 4000 rpm for 20 minutes. The size of the particles in the mixture was measured after 10 minutes and again after 15 minutes. After 20 minutes, the mixture had the consistency of ice cream. Deionized water (20 g.) was added and the mixture was mixed at 4000 rpm for another 30 seconds.

The formulation (70.1 g) that was recovered from the Eiger mill was placed in a beaker equipped with a mechanical stirrer and diluted with water (13.5 g), and Flexiverse 57:1 (7.78 g, Lot No. K99342, Sample No. RM4098, available from SunChemical), and Vinamul 18160 (6.86 g, Lot No. 106863, available from Vinamul LTD., England) were added and the suspension was stirred for 15 minutes. Keizen HP (2%), (0.12 g, Lot No. JFA43A, available from Kelco) was added and the suspension was stirred for 1 hour. The amount of the formulation at this point was 98.8 g.

The average particle size in the suspension was 11 microns. It was concluded that milling in excess of 10 minutes was not required. The simeconazole formulation contained slightly about 10% by weight simeconazole, and was ready for use for the treatment of seeds.

EXAMPLE 2

This example illustrates the treatment of soybean seeds with a seed treatment formulation that contains simeconazole.

Soybean seed (CSR2121 variety, available from Monsanto Company, St. Louis, Mo.), is placed in a rotostatic seed treatment device (available from Hege Equipment, Inc., Colwich, Kans.). A formulation containing about 10% by weight simeconazole, prepared as described in Example 1, is added to the coated seed at the rate of 2.5 ml/kg of seed, and the seed treatment device is operated according to the instructions provided in order to coat the seed with the formulation. The treatment provides seeds having a treatment rate of about 25 g of simeconazole per 100 kilograms of seeds.

EXAMPLE 3

This example shows a method of treating soybean seed with simeconazole or 1-(4-fluorophenyl)-2-(1H-1,2,4-triazole-1-yl)ethanone with and without *Bradyrhizobium* spp. inoculum.

Soybean seed (CSR$^{2121}$ variety, available from Monsanto Company, St. Louis, Mo.), is placed in a rotostatic seed treatment device (available from Hege Equipment, Inc., Colwich, Kans.). A spreader/sticker compound (such as, for example, Mollyflo®, available from Soygro (Pty) Ltd., Mooibank, Botchefstroom, South Africa) is added to the seed with agitation at the rate of 4 ml/kg of seed and distributed over the seed. A formulation containing simeconazole or 1-(4-fluorophenyl)-2-(1H-1,2,4-triazole-1-yl)ethanone as the active ingredient is added to the coated seed at the rate of 2 ml/kg of seed. Simeconazole can be prepared as described in Itoh, H. et al., *Chemical and Pharmaceutical Bulletin*, 8:1148–1153 (2000); Tsuda, M. et al., *Simeconazole (F-155), a novel systemic fungicide with broad-spectrum activity for seed treatment, The BCPC Conference—Pests & Diseases* 2000; and European Patent Publication No. 0 609 099 A1. The formulation is prepared to contain about 125 gm/liter of simeconazole or 1-(4-fluorophenyl)-2-(1H-1,2,4-triazole-1-yl)ethanone. The active formulation is added to the coated seed after addition of the spreader/sticker and during agitation of the seed.

For seeds that were to receive a coating of an inoculant, a peat-based *Bradyrhizobium* spp. formulation is added to the seeds immediately before planting by adding the inoculant formulation to the seed at a rate of 10 gm/kg of seed. The inoculant formulation can be added to the seed in a seed packet and thoroughly manually intermixed to contact all of the seed with the inoculant. The seed is then ready for planting.

The amount of the active ingredient that is added to the formulation can be sufficient for the concentration of the active in the formulation to be at any level that is desired. Commonly, the formulations are prepared so that the concentration of active ingredient in the formulation is 1.0 mg/kg, or 10 mg/kg, or 100 mg/kg, or even higher, if that is desirable. In fact, it is useful for the concentration of the fungicide to be at least about 100 mg/kg, and more desirable that it be present in a concentration of at least about 1% by weight, or higher. The compositions can be used as is, or they may be diluted by a carrier to any concentration that is useful for a particular application.

EXAMPLE 4

This illustrates the in vitro fungicidal activity of simeconazole, fluquinconazole, and azoxystrobin on strains of *Gaeumannomyces graminis*.

Fungal isolates of *Gaeumannoyces graminis* var. *tritici*, strains UK22A, 1-1-2-2, 1-1-2-3, 1-1-2-6, 1-1-2-8, 1-1-2-13, and 1-1-2-17, are cultivated for 6 to 14 days on a minimal media containing 17.5 g Czapek Dox broth (DIFCO), 7.5 g Bacto agar (DIFCO), 50 μl thiamine hydrochloride (c=1000 mg/kg, MERCK), and 50 μl biotin (c=1000 mg/kg, MERCK), made up to one liter with sterile deionized water.

In vitro assays are carried out by growing the isolates mentioned above in minimal medium containing 0, 0.01, 0.1, 1, and 100 mg/kg concentrations of simeconazole, or azoxystrobin (available from ZENECA LIMITED LIABILITY COMPANY UNITED KINGDOM 15 Stanhope Gate London ENGLAND W1Y 6LN, under the trade name AMISTAR®), or fluquinconazole (available from Aventis Crop Science under the trade name JOCKEY). Each of the fungicides is dissolved in methanol before it is added to the autoclaved minimal medium at 60° C., whereas for the control (0 mg/kg) only methanol is added.

The assay was performed by placing three mycelium plugs (diameter 5 mm) from the growing edge of the fungal cultures upside down in a triangular pattern onto the agar surface in a 55 mm-diameter petri dish (BIBBY STERILIN). This means that each petri dish contained 3 replicates for each concentration of the test compound.

After incubation for 4 days at 18° C. in the dark, the diameter of the mycelium growth was measured. If desired, $EC_{50}$ values can be calculated by fitting a log-logistic curve using statistical software available from SAS Institute, Inc., Cary, N.C.

The fungicidal activity of each of the tested fungicides was also calculated and reported as percent activity. The average diameter of the mycelium growth from the three plugs in the plate containing the control agar was measured ($D_{Avg\ Control}$), and the average diameter of the growth of the same mycelial strain in the three plugs on agar containing a fungicide, or combination of fungicides was also measured ($D_{Avg.FungicideX}$). The percent fungicidal activity was calculated as:

Percent Activity=$(((D_{Avg.Control}-5)-(D_{Avg.FungicideX}-5))/(D_{Avg.Control}-5))\times 100$ where diameters are reported in millimeters and 5 represents the diameter of the plug of inoculum. Thus, if there was no growth in the sample containing the fungicide, the activity would be reported as 100%. Whereas, if the diameter of the mycelia on the agar containing the fungicide was the same as that of the mycelia on the control agar—containing no fungicide—the percent activity would be reported as 0%. Accordingly, some amount of growth in the agar containing the fungicide, or combination of fungicides, but less than the growth on the control agar, would give a percent activity between 0 and 100%.

TABLE 1

Fungicidal activity of simeconazole on selected strains of *Gaeumannomyces graminis*.

| PATHOGEN (*Gaeumannomyces* gaminis strain no.) | ACTIVITIES OF SIMECONAZOLE AT VARIOUS CONCENTRATIONS (mg/kg) | | | | |
|---|---|---|---|---|---|
| | 0 | 0.01 | 0.1 | 1.0 | 10 |
| UK22A | 0 | 1.02 | 30.63 | 93.4 | 100 |
| 1-1-2-2 | 0 | 0 | 11.09 | 82.14 | 99.38 |
| 1-1-2-3 | 0 | 12.1 | 36.47 | 93.95 | 100 |

TABLE 1-continued

Fungicidal activity of simeconazole on selected strains of
*Gaeumannomyces graminis.*

| PATHOGEN (*Gaeumannomyces gaminis* strain no.) | ACTIVITIES OF SIMECONAZOLE AT VARIOUS CONCENTRATIONS (mg/kg) | | | | |
|---|---|---|---|---|---|
| | 0 | 0.01 | 0.1 | 1.0 | 10 |
| 1-1-2-6 | 0 | −6.25 | 22.5 | 93.75 | 100 |
| 1-1-2-8 | 0 | −16.74 | −2.71 | 86.88 | 100 |
| 1-1-2-13 | 0 | 3.28 | 6.35 | 78.07 | 100 |
| 1-1-2-17 | 0 | −1.27 | 9.34 | 88.96 | 100 |

TABLE 2

Fungicidal activity of azoxystrobin on selected strains of
*Gaeumannomyces graminis.*

| PATHOGEN (*Gaeumannomyces gaminis* strain no.) | ACTIVITIES OF AZOXYSTROBIN AT VARIOUS CONCENTRATIONS (mg/kg) | | | | |
|---|---|---|---|---|---|
| | 0 | 0.01 | 0.1 | 1.0 | 10 |
| UK22A | 0 | 4.06 | 10.66 | 14.55 | 93.23 |
| 1-1-2-2 | 0 | 40.04 | 51.95 | 72.28 | 100 |
| 1-1-2-3 | 0 | 6.05 | 10.59 | 43.87 | 100 |
| 1-1-2-6 | 0 | 2.5 | 11.04 | 24.17 | 93.75 |
| 1-1-2-8 | 0 | −3.62 | 14.48 | 45.48 | 100 |
| 1-1-2-13 | 0 | 3.28 | 6.35 | 78.07 | 100 |
| 1-1-2-17 | 0 | −1.27 | 9.34 | 88.96 | 100 |

TABLE 3

Fungicidal activity of fluquinconazole on selected strains of
*Gaeumannomyces graminis.*

| PATHOGEN (*Gaeumannomyces gaminis* strain no.) | ACTIVITIES OF FLUQUINCONAZOLE AT VARIOUS CONCENTRATIONS (mg/kg) | | | | |
|---|---|---|---|---|---|
| | 0 | 0.01 | 0.1 | 1.0 | 10 |
| UK22A | 0 | 7.95 | 99.15 | 100 | 100 |
| 1-1-2-2 | 0 | 7.19 | 93.43 | 100 | 100 |
| 1-1-2-3 | 0 | 22.52 | 100 | 100 | 100 |
| 1-1-2-6 | 0 | 5 | 100 | 100 | 100 |
| 1-1-2-8 | 0 | −11.31 | 92.53 | 100 | 100 |
| 1-1-2-13 | 0 | −1.43 | 95.08 | 100 | 100 |
| 1-1-2-17 | 0 | −4.88 | 92.78 | 100 | 100 |

The tests of the activity of the 3 fungicides on the 7 strains of *Gaeumannomyces gramminis* showed positive dose/response fungicidal activity for each of the 3 fungicides. Therefore, it was concluded that each of the fungicides, simeconazole, azoxystrobin and fluquinconazole, showed fungicidal activity against *Gaeumannomyces gramminis*.

EXAMPLE 5

This example illustrates a protocol for testing the effect on soybean yield and vigor of seed treatment prior to planting with simeconazole with and without an inoculant as compared with seeds having no treatment, seeds with only a sticking agent and an inoculant, and seeds that were treated with a commonly used pesticide combination with and without an inoculant and alone and in combination with simeconazole.

The following protocol provides a field trial that can be carried out to test the efficacy of soybean seed treatment with simeconazole as a function of several variables that are believed to be important for the present invention.

Soybean seeds of a selected variety are treated by applying Mollyflo® to the seeds in a rotostatic seed treatment machine (Hege machine) prior to seed packeting. An inoculant, if used, is added to seed envelopes in the field immediately prior to planting. In all seeds treated with simeconazole, the simeconazole is added to seed in a rotostatic seed-treating machine prior to the addition of Mollyflo®. Rival®/Allegiance® is added to seed in a rotostatic seed treating machine prior to planting. Rival® is a mixture of three fungicides, Allegiance® is a formulation of metalaxyl. Both are available from Gustafson. The following treatments can be used:

| TREATMENT NO. | DESCRIPTION |
|---|---|
| 1. | Untreated control |
| 2. | Seeds are treated with Mollyflo ® (4 ml/kg) and Inoculant (10 g/kg, applied at the time of planting). |
| 3. | Seeds are treated with Mollyflo ® (4 ml/kg), plus Rival ® (5 floz/cwt) and Allegiance ® (0.375 floz/cwt), plus Inoculant (10 g/kg, applied at the time of planting). |
| 4. | Seeds are treated with Mollyflo ® (4 ml/kg), plus 2 ml/kg of a simeconazole formulation (having 125 g/l of active agent), plus Inoculant (10 g/kg, applied at the time of planting). |
| 5. | Seeds are treated with Rival ® (5 floz/cwt) and Allegiance ® (0.375 floz/cwt). |
| 6. | Seeds are treated with 2 ml/kg of a simeconazole formulation (having 125 g/l of active agent). |
| 7. | Seeds are treated with Mollyflo ® (4 ml/kg), plus Rival ® (5 floz/cwt) and Allegiance ® (0.375 floz/cwt), plus 2 ml/kg of a simeconazole formulation (having 125 g/l of active agent), plus Inoculant (10 g/kg, applied at the time of planting). |
| 8. | Seeds are treated with Mollyflo ® (4 ml/kg), plus Rival ® (5 floz/cwt) and Allegiance ® (0.375 floz/cwt), plus 4 ml/kg of a simeconazole formulation (having 125 g/l of active agent), plus Inoculant (10 g/kg, applied at the time of planting). |

After the seeds have received the designated treatments, they are planted in 8-row plots with 15-inch row spacing and in rows of 50-ft. length on a 10'×50' plot. Stand counts are carried out at Vc-V1 (June 1) and at V3 stages (June 21). Plant vigor is reported according to a standard 1–9 scale, with 1 being worst and 9 being best and most vigorous. The percent canopy can be reported as percent of canopy closure where 100% is total coverage. Vigor and canopy determinations can be made at 50, 60, 71, 82, 92 and 102 days after planting. Days to maturity are counted from planting until 95% pod brown. Stand count, vigor, time to maturity, plant height, seed yield and seed size are measured as described above, and the efficacy of simecomazole treatment of soybean seeds can then be determined as a function of the presence or absence of inoculant, and can be compared versus comparable treatments with other, commonly used, fungicides. It is believed that the results obtained from a trial using this protocol support the conclusion that soybean seeds that had received treatment with simeconazole will show improved vigor and/or the yield as compared against soybeans for which the seeds did not have such treatment.

All references cited in this specification, including without limitation all papers, publications, patents, patent applications, presentations, texts, reports, manuscripts, brochures, books, internet postings, journal articles, periodicals, and the like, are hereby incorporated herein by reference in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed is:

1. A method of increasing the vigor and/or the yield of an agronomic plant comprising treating the plant or its propagation material with an effective amount of a triazole fungicide selected from the group consisting of amitrol, azaconazole, bitertanol, bromuconazole, climbazole, clotrimazole, cyproconazole, diclobutrazol, difenoconazole, diniconazole, diniconazole-M, epoxiconazole, etaconazole, fenbuconazole, fluquinconazole, fluotrimazole, flusilazole, flutriafol, furconazole, furconazole-cis, hexaconazole, imibenconazole, ipconazole, metconazole, myclobutanil, paclobutrazol, penconazole, propiconazole, quinconazole, simeconazole, tebuconazole, tetraconazole, triadimefon, triadimenol, triazbutil, 1-(4-fluorophenyl)-2-(1H-1,2,4-triazole-1-yl)ethanone, and mixtures thereof, or a strobilurin fungicide; and
    planting the treated propagation material and/or growing the treated plant in the absence of pest pressure by fungal plant pathogens against which the triazole, or strobilurin type fungicide is known to be active, and thereby increasing the vigor and/or the yield of the plant.

2. The method according to claim 1, wherein the fungicide comprises fluquinconazole, simeconazole, tebuconazole, tetraconazole, 1-(4-fluorophenyl)-2-(1H-1,2,4-triazole-1-yl)ethanone, or mixtures thereof.

3. The method according to claim 2, wherein the fungicide comprises fluquinconazole.

4. The method according to claim 2, wherein the fungicide comprises simeconazole.

5. The method according to claim 4, wherein the plant or its propagation material is further treated with silthiofam.

6. The method according to claim 2, wherein the fungicide comprises tebuconazole.

7. The method according to claim 2, wherein the fungicide comprises tetraconazole.

8. The method according to claim 2, wherein the fungicide comprises 1-(4-fluorophenyl)-2-(1H-1,2,4-triazole-1-yl)ethanone.

9. The method according to claim 1, wherein the fungicide comprises fluquinconazole and simeconazole.

10. The method according to claim 1, wherein the fungicide comprises fluquinconazole and azoxystrobin.

11. The method according to claim 1, wherein the fungicide comprises simeconazole and azoxystrobin.

12. The method according to claim 1, wherein the plant or its propagation material comprises seed and the seed is treated with an amount of the fungicide from about 0.1 gm/100 kg of seed to about 1,000 gm/100 kg of seed.

13. The method according to claim 12, wherein the seed is treated with fungicide in an amount of from about 2 gm/100 kg of seed to about 200 gm/100 kg of seed.

14. The method according to claim 13, wherein the seed is treated with fungicide in an amount of from about 10 gm/100 kg of seed to about 150 gm/100 kg of seed.

15. The method according to claim 14, wherein the seed is treated with fungicide in an amount of from about 20 gm/100 kg of seed to about 100 gm/100 kg of seed.

16. The method according to claim 1, wherein the agronomic plant is selected from the group consisting of corn, cereals, barley, rye, rice, vegetables, clovers, legumes, beans, peas, alfalfa, sugar cane, sugar beets, tobacco, cotton, rapeseed (canola), sunflower, safflower, and sorghum.

17. The method according to claim 16, wherein the agronomic crop comprises corn.

18. The method according to claim 1, wherein the agronomic plant is a member of the class Magnoliopsida.

19. The method according to claim 1, wherein the agronomic plant is a member of the order Fabales.

20. The method according to claim 1, wherein the agronomic plant is a member of the family Fabaceae.

21. The method according to claim 1, wherein the agronomic plant is a member of the sub-family Papilionoideae or Faboideae.

22. The method according to claim 1, wherein the agronomic plant is selected from the group consisting of *Pisum* spp., *Medicago* spp., *Arachis* spp., *Glycine* spp., *Vicia* spp., *Vigna* spp., trefoil, clovers and *Phaseolus* spp.

23. The method according to claim 1, wherein the agronomic plant is a soybean plant.

24. The method according to claim 1, wherein the step of treating the plant or its propagation material comprises treating a seed of the plant with an effective amount of the fungicide.

25. The method according to claim 24, wherein the seed is treated with an inoculant comprising *Azospirillium* spp, or *Rhizobium* spp., or *Bradyrhizobium* spp, or a mixture of *Rhizobium* spp and *Bradyrhizobium* spp, or a mixture of either *Rhizobium* spp or *Bradyrhizobium* spp with any other microorganisms.

26. The method according to claim 24, wherein the seed is treated with an inoculant comprising *Bradyrhizobium japonicum*.

27. The method according to claim 24, wherein the treatment of the seed of the plant comprises, in addition, treatment of the seed with a fungicide selected from the group consisting of fludioxonil, fluquinconazole, difenoconazole, captan, metalaxyl, carboxin and thiram.

28. The method according to claim 24, where the treatment of the seed comprises treatment with an inoculant comprising *Azospirillium* spp, or *Rhizobium* spp, or *Bradyrhizobium* spp, or a mixture of *Rhizobium* spp and *Bradyrhizobium* spp, or a mixture of either *Rhizobium* spp, or *Bradyrhizobium* spp with any other microorganisms.

29. The method according to claim 1, wherein the step of treating the plant or its propagation material comprises applying the fungicide to the foliage of the plant.

30. The method according to claim 29, wherein the agronomic plant is a member of the family Fabaceae.

31. The method according to claim 29, wherein the agronomic plant is a member of the sub-family Papilionoideae or Faboideae.

32. The method according to claim 29, wherein the agronomic plant is selected from the group consisting of *Pisum* spp, *Medicago* spp, *Arachis* spp, *Glycine* spp, *Vicia* spp, *Vigna* spp, trefoil, clovers and *Phaseolus* spp.

33. The method according to claim 29, wherein the seed possesses a transgenic event providing the plant with resistance to a herbicide selected from the group consisting of glyphosate, glufosinate, imidazolinone, and sulfonylurea and the treatment comprises foliar application of said herbicide.

34. The method according to claim 29, wherein the seed possesses a transgenic event providing the plant with resistance to a herbicide and the step of applying the fungicide to the foliage of the plant comprises the application of the fungicide in combination with said herbicide.

35. The method according to claim 34, wherein the herbicide is glyphosate.

36. The method according to claim 1, wherein the plant propagation material comprises a seed and wherein the seed possesses a transgenic event providing the plant with resistance to a herbicide and the treatment comprises foliar application of said herbicide.

37. The method according to claim 36, wherein the herbicide is selected from the group consisting of glyphosate, glufosinate, imidazolinone, and sulfonylurea.

38. The method according to claim 1, wherein the treatment comprises treating the seed of the plant with an inoculant selected from the group consisting of *Azospirillium* spp, or *Rhizobium* spp, or *Bradyrhizobium* spp, or a mixture of *Rhizobium* spp and *Bradyrhizobium* spp, or a mixture of either *Rhizobium* spp, or *Bradyrhizobium* spp with any other microorganisms, and further includes foliar treatment of the plant with an active agent.

39. The method according to claim 38, wherein the seed possesses a transgenic event providing the plant with resistance to a herbicide selected from the group consisting of glyphosate, glufosinate, imidazolinone, and sulfonylurea and the treatment further comprises foliar application of said herbicide.

40. The method according to claim 1, wherein the strobilurin fungicide is selected from the group consisting of azoxystrobin, dimoxystrobin, famoxadone, kresoxim-methyl, metominostrobin, picoxystrobin, pyraclostrobin, trifloxystrobin, and mixtures thereof.

41. A method of increasing the vigor and/or the yield of an agronomic plant comprising treating the plant or its propagation material with a silthiofam-type fungicide and an effective amount of a triazole fungicide, or a strobilurin fungicide; and
   planting the treated propagation material and/or growing the treated plant in the absence of pest pressure by fungal plant pathogens against which the triazole, or strobilurin type fungicide is known to be active, and thereby increasing the vigor and/or the yield of the plant.

42. The method according to claim 41, wherein the fungicide comprises a triazole fungicide having a halogen-substituted phenyl group that is linked to a 1,2,4-triazole group.

43. The method according to claim 41, wherein the fungicide comprises a triazole fungicide selected from the group consisting of amitrol, azaconazole, bitertanol, bromuconazole, climbazole, clotrimazole, cyproconazole, diclobutrazol, difenoconazole, diniconazole, diniconazole-M, epoxiconazole, etaconazole, fenbuconazole, fluquinconazole, fluotrimazole, flusilazole, flutriafol, furconazole, furconazole-cis, hexaconazole, imibenconazole, ipconazole, metconazole, myclobutanil, paclobutrazol, penconazole, propiconazole, quinconazole, simeconazole, tebuconazole, tetraconazole, triadimefon, triadimenol, triazbutil, triticonazole, 1-(4-fluorophenyl)-2-(1H-1,2,4-triazole-1-yl)ethanone, and mixtures thereof.

44. The method according to claim 41, wherein the fungicide comprises fluquinconazole, simeconazole, tebuconazole, tetraconazole, triticonazole, 1-(4-fluorophenyl)-2-(1H-1,2,4-triazole-1-yl)ethanone, or mixtures thereof.

45. The method according to claim 41, wherein the fungicide comprises fluquinconazole.

46. The method according to claim 41, wherein the fungicide comprises simeconazole.

47. The method according to claim 41, wherein the fungicide comprises tebuconazole.

48. The method according to claim 41, wherein the fungicide comprises tetraconazole.

49. The method according to claim 41, wherein the fungicide comprises triticonazole.

50. The method according to claim 41, wherein the fungicide comprises 1-(4-fluorophenyl)-2-(1H-1,2,4-triazole-1-yl)ethanone.

51. The method according to claim 41, wherein the fungicide comprises fluquinconazole and simeconazole.

52. The method according to claim 41, wherein the fungicide comprises fluquinconazole and azoxystrobin.

53. The method according to claim 41, wherein the fungicide comprises simeconazole and azoxystrobin.

54. The method according to claim 41, wherein the plant or its propagation material comprises seed and the seed is treated with an amount of the fungicide from about 0.1 gm/100 kg of seed to about 1,000 gm/100 kg of seed.

55. The method according to claim 41, wherein the seed is treated with fungicide in an amount of from about 2 gm/100 kg of seed to about 200 gm/100 kg of seed.

56. The method according to claim 41, wherein the seed is treated with fungicide in an amount of from about 10 gm/100 kg of seed to about 150 gm/100 kg of seed.

57. The method according to claim 41, wherein the seed is treated with fungicide in an amount of from about 20 gm/100 kg of seed to about 100 gm/100 kg of seed.

58. The method according to claim 41, wherein the agronomic plant is selected from the group consisting of corn, cereals, barley, rye, rice, vegetables, clovers, legumes, beans, peas, alfalfa, sugar cane, sugar beets, tobacco, cotton, rapeseed (canola), sunflower, safflower, and sorghum.

59. The method according to claim 41, wherein the agronomic crop comprises corn.

60. The method according to claim 41, wherein the agronomic plant is a member of the class Magnoliopsida.

61. The method according to claim 41, wherein the agronomic plant is a member of the order Fabales.

62. The method according to claim 41, wherein the agronomic plant is a member of the family Fabaceae.

63. The method according to claim 41, wherein the agronomic plant is a member of the sub-family Papilionoideae or Faboideae.

64. The method according to claim 41, wherein the agronomic plant is selected from the group consisting of *Pisum* spp., *Medicago* spp., *Arachis* spp., *Glycine* spp., *Vicia* spp., *Vigna* spp., trefoil, clovers and *Phaseolus spp.*

65. The method according to claim 41, wherein the agronomic plant is a soybean plant.

66. The method according to claim 41, wherein the step of treating the plant or its propagation material comprises treating a seed of the plant with an effective amount of the fungicide.

67. The method according to claim 66, wherein the seed is treated with an inoculant comprising *Azospirillium* spp, or *Rhizobium* spp., or *Bradyrhizobium* spp, or a mixture of *Rhizobium* spp and *Bradyrhizobium* spp, or a mixture of either *Rhizobium* spp or *Bradyrhizobium* spp with any other microorganisms.

68. The method according to claim 66, wherein the seed is treated with an inoculant comprising *Bradyrhizobium japonicum*.

69. The method according to claim 66, wherein the treatment of the seed of the plant comprises, in addition, treatment of the seed with a fungicide selected from the group consisting of fludioxonil, fluquinconazole, difenoconazole, captan, metalaxyl, carboxin and thiram.

70. The method according to claim 66, where the treatment of the seed comprises treatment with an inoculant comprising *Azospirillium* spp, or *Rhizobium* spp, or *Bradyrhizobium* spp, or a mixture of *Rhizobium* spp and *Bradyrhizobium* spp, or a mixture of either *Rhizobium* spp, or *Bradyrhizobium* spp with any other microorganisms.

71. The method according to claim 41, wherein the step of treating the plant or its propagation material comprises applying the fungicide to the foliage of the plant.

72. The method according to claim 71, wherein the agronomic plant is a member of the family Fabaceae.

73. The method according to claim 71, wherein the agronomic plant is a member of the sub-family Papilionoideae or Faboideae.

74. The method according to claim 71, wherein the agronomic plant is selected from the group consisting of *Pisum* spp, *Medicago* spp, *Arachis* spp, *Glycine* spp, *Vicia* spp, *Vigna* spp, trefoil, clovers and *Phaseolus* spp.

75. The method according to claim 71, wherein the seed possesses a transgenic event providing the plant with resistance to a herbicide selected from the group consisting of glyphosate, glufosinate, imidazolinone, and sulfonylurea and the treatment comprises foliar application of said herbicide.

76. The method according to claim 71, wherein the seed possesses a transgenic event providing the plant with resistance to a herbicide and the step of applying the fungicide to the foliage of the plant comprises the application of the fungicide in combination with said herbicide.

77. The method according to claim 76, wherein the herbicide is glyphosate.

78. The method according to claim 41, wherein the plant propagation material comprises a seed and wherein the seed possesses a transgenic event providing the plant with resistance to a herbicide and the treatment comprises foliar application of said herbicide.

79. The method according to claim 78, wherein the herbicide is selected from the group consisting of glyphosate, glufosinate, imidazolinone, and sulfonylurea.

80. The method according to claim 41, wherein the treatment comprises treating the seed of the plant with an inoculant selected from the group consisting of *Azospirillium* spp, or *Rhizobium* spp, or *Bradyrhizobium* spp, or a mixture of *Rhizobium* spp and *Bradyrhizobium* spp, or a mixture of either *Rhizobium* spp, or *Bradyrhizobium* spp with any other microorganisms, and further includes foliar treatment of the plant with an active agent.

81. The method according to claim 80, wherein the seed possesses a transgenic event providing the plant with resistance to a herbicide selected from the group consisting of glyphosate, glufosinate, imidazolinone, and sulfonylurea and the treatment further comprises foliar application of said herbicide.

82. The method according to claim 41, wherein the strobilurin fungicide is selected from the group consisting of azoxystrobin, dimoxystrobin, famoxadone, kresoxim-methyl, metominostrobin, picoxystrobin, pyraclostrobin, trifloxystrobin, and mixtures thereof.

* * * * *

UNITED STATES PATENT AND TRADEMARK OFFICE
CERTIFICATE OF CORRECTION

PATENT NO. : 7,098,170 B2
APPLICATION NO. : 10/081023
DATED : August 29, 2006
INVENTOR(S) : Jawed Asrar, Ernest F. Sanders and Yiwei Ding It is certified that error appears in the above-identified patent and that said Letters Patent is hereby corrected as shown below:

Column 3:
Lines 20-21, 24-25 and 32 replace the terms "Gaeumannoyces graminis" with the terms -- Gaeumannomyces --.

Column 4:
Lines 38-39, 43 and 48 replace the terms "Gaeumannoyces graminis" with the terms -- Gaeumannomyces --.

Column 5:
Lines 7, 20, 25, 27-28, 32 and 61 replace the terms "Gaeumannoyces graminis" with the terms -- Gaeumannomyces --.

Column 6:
Line 18 replace the terms "Gaeumannoyces graminis" with the terms -- Gaeumannomyces --.

Column 8:
Line 16 replace the terms "Gaeumannoyces graminis" with the terms -- Gaeumannomyces --.

Column 13:
Lines 2-3 replace the terms "butyidimethylsily, pentyidlmethylsilyl," with the terms -- butyldimethylsiyl, pentyldimethylsiyl,--.

Column 32:
Line 62 replace the terms "Keizen HP" with the terms -- Kelzen HP --.

Signed and Sealed this

Fifth Day of June, 2007

JON W. DUDAS
*Director of the United States Patent and Trademark Office*